US011161834B2

(12) United States Patent
Stewart et al.

(10) Patent No.: US 11,161,834 B2
(45) Date of Patent: Nov. 2, 2021

(54) METHODS OF MANUFACTURING OF NIRAPARIB

(71) Applicant: TESARO, INC., Waltham, MA (US)

(72) Inventors: Alistair Stewart, Waltham, MA (US); Anthony Joseph Toto, Waltham, MA (US); Frank Xing Chen, Plainsboro, NJ (US); George Wu, Waltham, MA (US)

(73) Assignee: Tesaro, Inc., Waltham, MA (US)

( * ) Notice: Subject to any disclaimer, the term of this patent is extended or adjusted under 35 U.S.C. 154(b) by 0 days.

(21) Appl. No.: 16/608,059

(22) PCT Filed: Apr. 24, 2018

(86) PCT No.: PCT/US2018/029131
§ 371 (c)(1),
(2) Date: Oct. 24, 2019

(87) PCT Pub. No.: WO2018/200517
PCT Pub. Date: Nov. 1, 2018

(65) Prior Publication Data
US 2020/0055837 A1    Feb. 20, 2020

Related U.S. Application Data

(60) Provisional application No. 62/489,387, filed on Apr. 24, 2017, provisional application No. 62/489,415, filed on Apr. 24, 2017.

(51) Int. Cl.
C07D 401/10    (2006.01)

(52) U.S. Cl.
CPC ................... *C07D 401/10* (2013.01)

(58) Field of Classification Search
CPC .................................................. C07D 401/10
See application file for complete search history.

(56) References Cited

U.S. PATENT DOCUMENTS

| | | | |
|---|---|---|---|
| 6,537,746 B2 | 3/2003 | Arnold et al. |
| 7,169,592 B2 | 1/2007 | Yamada et al. |
| 7,199,147 B2 | 4/2007 | Imazaki et al. |
| 8,071,623 B2 | 12/2011 | Jones et al. |
| 8,129,377 B2 | 3/2012 | Watanabe et al. |
| 8,436,185 B2 | 5/2013 | Foley et al. |
| 9,580,407 B2 | 2/2017 | Chung et al. |
| 9,738,915 B2 | 8/2017 | Bulger et al. |
| 10,407,702 B2 | 9/2019 | Bulger et al. |
| 10,435,386 B2 | 10/2019 | Chung et al. |
| 10,815,214 B2 | 10/2020 | Chung et al. |
| 2008/0167345 A1 | 7/2008 | Jones et al. |
| 2008/0213845 A1 | 9/2008 | Fotheringham et al. |
| 2010/0222326 A1 | 9/2010 | Kenda et al. |
| 2010/0285541 A1 | 11/2010 | Saville et al. |
| 2010/0286203 A1 | 11/2010 | Foley et al. |
| 2010/0295541 A1 | 11/2010 | Sano |
| 2012/0245172 A1 | 9/2012 | Galley et al. |
| 2015/0299167 A1 | 10/2015 | Chung et al. |
| 2018/0311224 A1 | 11/2018 | Hedley et al. |
| 2020/0016142 A1 | 1/2020 | McGurk et al. |
| 2020/0017462 A1 | 1/2020 | Wu et al. |
| 2021/0008053 A1 | 1/2021 | Sun et al. |

FOREIGN PATENT DOCUMENTS

| | | |
|---|---|---|
| CN | 106432055 | 2/2017 |
| CN | 106496187 | 3/2017 |
| EP | 2007733 | 5/2016 |
| EP | 2928473 | 6/2017 |
| EP | 2928865 | 4/2018 |
| WO | WO 9522625 | 8/1995 |
| WO | WO 9700078 | 1/1997 |
| WO | WO 9735966 | 10/1997 |
| WO | WO 9827230 | 6/1998 |
| WO | WO 0042651 | 7/2000 |
| WO | WO 2001/062726 | 8/2001 |
| WO | WO 0175767 | 10/2001 |
| WO | WO 2002085838 | 10/2002 |
| WO | WO 2007113596 | 10/2007 |
| WO | WO 2008/027466 | 3/2008 |
| WO | WO 2008084261 | 7/2008 |
| WO | WO 2009087381 | 7/2009 |
| WO | WO 2010099501 | 9/2010 |
| WO | WO 2012024104 | 2/2012 |
| WO | WO 2012/074126 | 6/2012 |
| WO | WO 2012/107850 | 8/2012 |
| WO | WO 2012/168260 | 12/2012 |
| WO | WO 2014088983 | 6/2014 |
| WO | WO 2014088984 | 6/2014 |
| WO | WO 2016094391 | 6/2016 |
| WO | WO 2018200517 | 11/2018 |
| WO | WO 2018208968 | 11/2018 |
| WO | WO 2018213732 | 11/2018 |
| WO | WO 2019067634 | 4/2019 |

(Continued)

OTHER PUBLICATIONS

Dakin Science of Synthesis 2007, 20, 608.*
Hu "A general and efficient approach to 2H-indazoles and 1H-pyrazoles through copper-catalyzed intramolecular N-N bond formation under mild conditions" Chem. Commun., 2011, 47, 10133-10135.*
Tehrani Science of Synthesis, (2004) 27, 245.*
Hansch "Survey of Hammett Substituent Constants and Resonance and Field Parameters" Chem. Rev. 1991, 97, 165-195.*
AU Office Action in Australian Appln. No. 2018258274, dated Apr. 20, 2020, 11 pages.
Chung et al., "Process Development of C—N Cross-Coupling and Enantioselective Biocatalytic Reactions for the Asymmetric Synthesis of Niraparib," Org. Process Res. Dev., 2014, 18(1):215-227.
Wallace et al., "Development of a Fit-for-Purpose Large-Scale Synthesis of an Oral PARP Inhibitor," Org. Process Res. Dev., 2011, 15(4):831-840.

(Continued)

*Primary Examiner* — David K O'Dell
(74) *Attorney, Agent, or Firm* — Fish & Richardson P.C.

(57) ABSTRACT

Disclosed herein are methods and processes of preparing niraparib and pharmaceutically acceptable salts thereof, and intermediates and their salts useful for the synthesis of niraparib.

7 Claims, 3 Drawing Sheets

(56) References Cited

FOREIGN PATENT DOCUMENTS

| WO | WO 2019067978 | 4/2019 |
|---|---|---|
| WO | WO 2019071123 | 4/2019 |
| WO | WO 2019133697 | 7/2019 |
| WO | WO 2019152989 | 8/2019 |

OTHER PUBLICATIONS

International Preliminary Report on Patentability dated Oct. 29, 2019 for PCT/US2018/029131.
International Search Report dated Aug. 1, 2018 for PCT/US2018/029131.
Written Opinion of the International Searching Authority dated Aug. 1, 2018 for PCT/US2018/029131.
ambinter.com [online], "Biological Clusters", Ambinter, Feb. 2, 2007, retrieved on Feb. 12, 2021, retrieved from URL <"http://web/archive.org/web/20070202005900/http://www.ambinter.com/">, 1 page.
Antilla et al., "Copper-Diamine-Catalyzed N-Acylation of Pyrroles, Pyrazoles, Indazoles, Imidazoles and Triazoles", The Journal of Organic Chemistry, 2004, 69(17):5578-5587.
Bhat et al., "A mild and selective method for N-dealkylation of tertiary amines", Tetrahedron Letters, 2004, 45(43):7983-7985.
Colpaert et al., "Asymmetric synthesis of chiral N-sulfinyl 3-alkyl- and 3-arylpiperidines by α-alkylation of N-sulfinyl imidates with 1-chloro-3-iodopropane", Journal of Organic Chemistry, Dec. 2010, 76(1):234-244.
Devos et al., "Practical limits of function prediction", Proteins: Structure, Function and Genetics, Aug. 2000, vol. 41:98-107.
Doherty et al., "Discovery of diphenyl lactam derivatives as N-type calcium channel blockers", Bioorganic & Medicinal Chemistry Letters, 2012, 22(4):1716-1718.
Jones et al., "Discovery of 2-[4-[(3S)-Piperidin-3-yl]-2H-indazole-7-carboxamide (MK-4827): A Novel Oral Poly(ADP-ribose) polymerase (PARP) Inhibitor Efficacious in BRCA-1 and -2 Mutant Tumors," Journal of Medicinal Chemistry, 2009, 52(22):7170-7185.
Kisselev, "Polypeptide Release Factors in Prokaryotes and Eukaryotes: Same Function, Different Structure", Structure, Jan. 2002,10(1):8-9.
Olaffson et al., "A New Reagent for the Selective, High-Yield N-Dealkylation of Tertiary Amines: Improved Syntheses of Naltrexone and Nalbuphine", The Journal of Organic Chemistry, 1984, 49(11)2081-2082.
Pontiki et al., "Quantitative structure activity relationships (QSAR) of substituted (S)-phenylpiperidines as preferential dopamine autoreceptor antagonists.", Journal of Enzyme Inhibition and Medicinal Chemistry, 2005, 20(1):5-12.
STN—Chemical database Registry entry RN 1088181-79-6 for N-(4-methoxyphenyl)-1H-Indazole-7-carboxamide, Entered STN: Dec. 22, 2008.
STN—Chemical database Registry entry RN 1147378-81-1 for N-(1,1-dimethylpropyl)-1H-Indazole-7-carboxamide, Entered STN: May 19, 2009.
STN—Chemical database Registry entry RN 1209934-80-4 for N-(1-phenylethyl)-1H-Indazole-7-carboxamide, Entered STN: Mar. 15, 2010.
web.archive.org [online], "Screening Compounds", Jun. 30, 2007, retrieved on Feb. 11, 2021, retrieved from URL <"http://web.archive.org/web/20070630171813/http://www.enamine.net/index.php?option=com_content&task=view&id=22&menuid=51&PHPSESSID=64a4f248f69d671a413f487bb62c4d90">, 2 pages.
Whisstock et al., "Prediction of protein function from protein sequence and structure", Quarterly Reviews of Biophysics, 2003, 36(3):307-340.
Witkowski et al., "Conversion of a beta-ketoacyl synthase to a malonyl decarboxylase by replacement of the active-site cysteine with glutamine", Biochemistry, Sep. 1999, 38(36):11643-11650.
Altschul et al., "Basic local alignment search tool," J. Mol. Biol., 1990, 215:403-410.
Altschul et al., "Gapped BLAST and PSI-BLAST: a new generation of protein database search programs," Nucleic Acids Res., 1977, 3389-3402.
Black et al., "Creation of drug-specific herpes simplex virus type 1 thymidine kinase mutants for gene therapy," Proc Natl Acad Sci USA, 1996, 93:3525-3529.
Botstein et al., "Strategies and applications of in vitro mutagenesis," Science, 1985, 229:1193-1201.
Caldwell et al., "Mutagenic PCR," PCR Methods Appl., 1994, 3:S136-S140.
Carter, "Site-directed mutagenesis," Biochem. J., 1986, 237:1-7.
Christians et al., "Directed evolution of thymidine kinase for AZT phosphorylation using DNA family shuffling," Nature Biotech, 1999, 17:259-264.
Crameri et al., "DNA shuffling of a family of genes from diverse species accelerates directed evolution," Nature, 1998, 391:288-291.
Crameri et al., "Improved green fluorescent protein by molecular evolution using DNA shuffling," Nature Biotech, 1996, 14:315-319.
Crameri et al., "Molecular evolution of an arsenate detoxification pathway by DNA shuffling," Nature Biotech, 1997, 15:436-438.
Dale et al., "Oligonucleotide-directed random mutagenesis using the phosphorothioate method," Methods Mol. Biol., 1996, 57:369-74.
Henikoff and Henikoff, "Amino acid substitution matrices from protein blocks," Proc. Natl. Acad. Sci. USA, 1989, 89: 10915.
Holme et al., "Efficient asymmetric synthesis of chiral amines by combining transaminase and pyruvate decarboxylase," 2008, Chem BioChem, 9:363-365.
Iwasaki et al., "Microbial synthesis of chiral amines by (R)-specific transamination with Arthrobacter sp. KNK168," Appl. Microbiol. Biotechnol, 2006, 69:499-505.
Koszelewski et al., "Asymmetric Synthesis of Optically Pure Pharmacologically Relevant Amines Employing ω-Transaminases," Adv. Syn. Catal., 2008, 350:2761-2766.
Koszelewski et al., "Synthesis of 4-phenylpyrrolidin-2-one via dynamic kinetic resolution catalyzed by ω-transaminases," J . Mol. Catal. B-Enzym., 2009, 60:191-194.
Kramer et al., "Different base/base mismatches are corrected with different efficiencies by the methyl-directed DNA mismatch-repair system of E. coli," Cell, 1984, 38:879-887.
Ling, et al., "Approaches to DNA mutagenesis: an overview," Anal. Biochem., 1997, 254(2):157-78.
Maligres et al., "A soluble copper(I) source and stable salts of volatile ligands for copper-catalyzed C-X couplings," J. Org. Chem., 2012, 77:7646-7651.
Minshull et al., "Protein evolution by molecular breeding," Curr Opin Chem Biol, 1999, 3:284-290.
Needleman and Wunsch, "A general method applicable to the search for similarities in the amino acid sequence of two proteins," J . Mol. Biol., 1970, 48:443.
Pearson and Lipman, "Improved tools for biological sequence comparison," Proc. Natl. Acad. Sci. USA, 1988, 85:2444.
Savile et al, "Biocatalytic asymmetric synthesis of chiral amines from ketones applied to sitagliptin manufacture," Science, 2010, 329(5989):305-9.
Shin et al., "Comparison of the omega-transaminases from different microorganisms and application to production of chiral amines," Biosci. Biotechnol. Biochem., 2001, 65: 1782-1788.
Smith and Waterman, "Comparison of Biosequences," Adv. Appl. Math., 1981, 2:482.
Smith, "In vitro mutagenesis," Ann. Rev. Genet., 1985, 19:423-462.
Stemmer, "DNA shuffling by random fragmentation and reassembly: in vitro recombination for molecular evolution," Proc Natl Acad Sci USA, 1994, 91:10747-10751.
Stemmer, "Rapid evolution of a protein in vitro by DNA shuffling," Nature, 1994, 370:389-391.
Streitwieser et al., "Introduction to Organic Chemistry, 2d ed.," Macmillan Publishing Company, 1981, 169-171.
Van Ophem et al., "Substrate inhibition of D-amino acid transaminase and protection by salts and by reduced nicotinamide adenine dinucleotide: isolation and initial characterization of a pyridoxo intermediate related to inactivation," Biochemistry, 1998, 37(9):2879-88.

(56) References Cited

OTHER PUBLICATIONS

Wells et al., "Cassette mutagenesis: an efficient method for generation of multiple mutations at defined sites," Gene, 1985, 34:315-323.

Zhang et al., "Directed evolution of a fucosidase from a galactosidase by DNA shuffling and screening," Proc Natl Acad Sci USA, 1997, 94:4504-4509.

Zhao et al., "Molecular evolution by staggered extension process (StEP) in vitro recombination," Nat. Biotechnol., 1998, 16:258-261.

\* cited by examiner

METHODS OF MANUFACTURING OF NIRAPARIB

CROSS REFERENCE TO RELATED APPLICATIONS

This application is a 35 U.S.C. § 371 National Stage Application of International Application No. PCT/US18/29131, filed Apr. 24, 2018, which claims the benefit of U.S. Provisional Application No. 62/489,387, filed Apr. 24, 2017, and U.S. Provisional Application No. 62/489,415, filed Apr. 24, 2017, each of which is incorporated herein by reference in their entirety.

SUMMARY OF THE INVENTION

Niraparib is an orally active and potent poly (ADP-ribose) polymerase, or PARP, inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436,185. Methods of making niraparib and pharmaceutically acceptable salts thereof are disclosed in International Publication Nos. WO2014/088983 and WO2014/088984. Methods to treat cancer with niraparib and pharmaceutically acceptable salts thereof are disclosed in U.S. Provisional Patent Application Nos. 62/356,461, 62/402,427, and 62/470,141. The contents of each of the foregoing references are incorporated herein by reference in their entirety.

PARP is a family of proteins involved in many functions in a cell, including DNA repair, gene expression, cell cycle control, intracellular trafficking and energy metabolism. PARP proteins play key roles in single strand break repair through the base excision repair pathway. PARP inhibitors have shown activity as a monotherapy against tumors with existing DNA repair defects, such as BRCA1 and BRCA2, and as a combination therapy when administered together with anti-cancer agents that induce DNA damage.

Despite several advances in treatment of ovarian cancer, most patients eventually relapse, and subsequent responses to additional treatment are often limited in duration. Women with germline BRCA1 or BRCA2 mutations have an increased risk for developing high grade serous ovarian cancer (HGSOC), and their tumors appear to be particularly sensitive to treatment with a PARP inhibitor. In addition, published scientific literature indicates that patients with platinum sensitive HGSOC who do not have germline BRCA1 or BRCA2 mutations may also experience clinical benefit from treatment with a PARP inhibitor.

Disclosed herein are methods and processes of preparing niraparib and pharmaceutically acceptable salts thereof, and intermediates and their salts useful for the synthesis of niraparib.

In one aspect, disclosed herein is a process for preparing a compound of Formula (1),

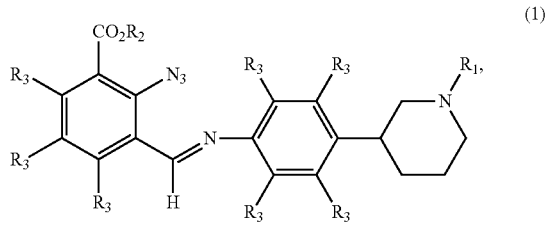

or a salt thereof, comprising: contacting a compound of Formula (2),

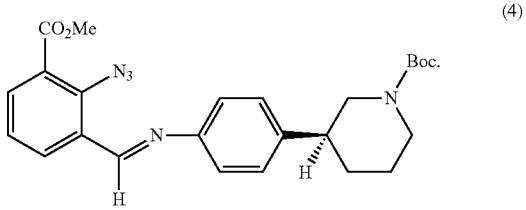 [SMILES: COC(=O)c1cccc(/C=N/c2ccc([C@@H]3CCCN(C(=O)OC(C)(C)C)C3)cc2)c1N=[N+]=[N-]]

or a salt thereof, with a compound of Formula (3), $$R_3 \quad R_3 \quad R_1 \tag{3}$$

$H_2N$ —

$R_3 \quad R_3$ or a salt thereof, wherein: $R_1$ is H or an amine protecting group; $R_2$ is H, $C_{1-10}$ alkyl, $C_{1-10}$ haloalkyl, or aryl; and each $R_3$ is independently H, halogen, $C_{1-10}$ alkyl, $C_{1-10}$ haloalkyl, or aryl. In some embodiments, the contacting results in formation of a water molecule.

In some embodiments, the contacting is in presence of an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphonic acid, sulfuric acid, nitric acid, phosphoric acid, hydrochloric acid, ethane sulfonic acid (ESA), or any combination thereof. In some embodiments, the acid is TFA.

In some embodiments, $R_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc).

In some embodiments, $R_2$ is $C_{1-10}$ alkyl. In some embodiments, $R_2$ is methyl. In some embodiments, each $R_3$ is H.

In some embodiments, the compound of Formula (1) or salt thereof has a structure of Formula (4):

In some embodiments, the compound of Formula (1) has a structure of Formula (4).

In another aspect, disclosed herein is a process for preparing a compound of Formula (5),

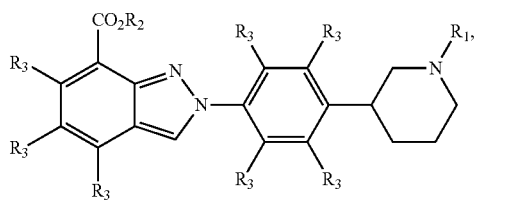
(5)

or a salt thereof, comprising: contacting a compound of Formula (1),

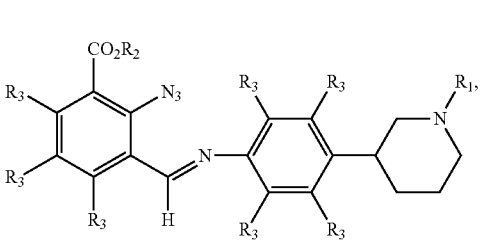
(1)

or a salt thereof, with a catalyst, wherein: $R_1$ is H or an amine protecting group; $R_2$ is H, $C_{1-10}$ alkyl, $C_{1-10}$ haloalkyl, or aryl; and each $R_3$ is independently H, halogen, $C_{1-10}$ alkyl, $C_{1-10}$ haloalkyl, or aryl.

In some embodiments, the catalyst comprises a Lewis acid, or a solvate thereof. In some embodiments, the Lewis acid has a formula of MXn, wherein M is Cu, Zn, B, Ti, Fe, Ni, Co, Al, or Ag, wherein X is halide, triflate, phosphate, fluorophosphate, or acetate, and wherein n is 1, 2, 3, or 4. In some embodiments, the M is Cu. In some embodiments, the Lewis acid is a copper salt. In some embodiments, the copper salt is copper(II) trifluoromethanesulfonate ($Cu(OTf)_2$).

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF.

In some embodiments, $R_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc).

In some embodiments, $R_2$ is $C_{1-10}$ alkyl. In some embodiments, $R_2$ is methyl. In some embodiments, each $R_3$ is H.

In some embodiments, the compound of Formula (5) or salt thereof has a structure of Formula (6):

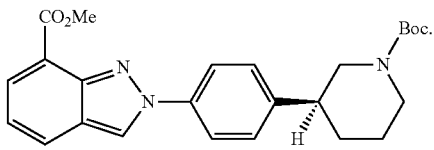
(6)

In some embodiments, the compound of Formula (5) has a structure of Formula (6).

In another aspect, disclosed herein is a process for preparing a salt of Formula (7),

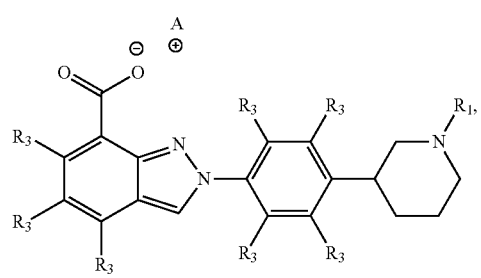
(7)

comprising: contacting a compound of Formula (5),

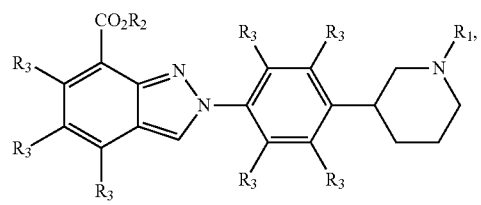
(5)

or a salt thereof, with a metal hydroxide, wherein: $R_1$ is H or an amine protecting group; $R_2$ is H, $C_{1-10}$ alkyl, $C_{1-10}$ haloalkyl, or aryl; each $R_3$ is independently H, halogen, $C_{1-10}$ alkyl, $C_{1-10}$ haloalkyl, or aryl; and A is a cation.

In some embodiments, the cation is an inorganic or organic cation. In some embodiments, the cation is a metal cation. In some embodiments, the metal cation is an alkali metal cation. In some embodiments, the alkali metal cation is lithium cation, sodium cation, potassium cation, rubidium cation, caesium cation, or francium cation. In some embodiments, the alkali metal cation is lithium cation.

In some embodiments, $R_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc).

In some embodiments, $R_2$ is $C_{1-10}$ alkyl. In some embodiments, $R_2$ is methyl. In some embodiments, each $R_3$ is H.

In some embodiments, the salt of Formula (7) has a structure of Formula (8):

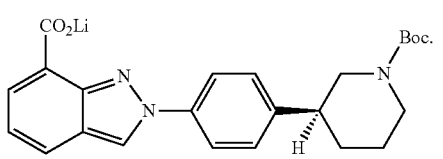
(8)

In another aspect, disclosed herein is a process for preparing a compound of Formula (9),

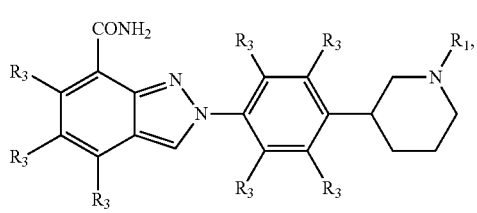
(9)

or a salt thereof, comprising: contacting a compound of Formula (7),

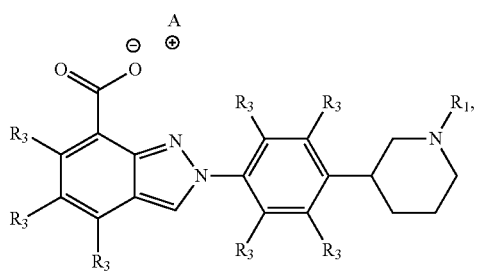
(7)

or a salt thereof, with a coupling reagent and ammonium hydroxide, wherein: $R_1$ is H or an amine protecting group; $R_2$ is H, $C_{1-10}$ alkyl, $C_{1-10}$ haloalkyl, or aryl; each $R_3$ is independently H, halogen, $C_{1-10}$ alkyl, $C_{1-10}$ haloalkyl, or aryl; and A is a cation.

In some embodiments, the cation is an inorganic or organic cation. In some embodiments, the cation is a metal cation. In some embodiments, the metal cation is an alkali metal cation. In some embodiments, the alkali metal cation is lithium cation, sodium cation, potassium cation, rubidium cation, caesium cation, or francium cation. In some embodiments, the alkali metal cation is lithium cation.

In some embodiments, the coupling reagent is carbonyldiimidazole (CDI), N,N'-Dicyclohexylcarbodiimide (DCC), 3-(diethoxyphosphoryloxy)-1,2,3-benzotriazin-4(3H)-one (DEPBT), N,N'-Diisopropylcarbodiimide, 1-[Bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), 1-Hydroxy-7-azabenzotriazole (HOAt), Hydroxybenzotriazole (HOBt), 7-Azabenzotriazol-1-yloxy)tripyrrolidinophosphonium hexafluorophosphate (PyAOP), or benzotriazol-1-yl-oxytripyrrolidinophosphonium hexafluorophosphate (PyBOP). In some embodiments, the coupling reagent is CDI.

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises DMF.

In some embodiments, the contacting is in presence of an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphonic acid, sulfuric acid, nitric acid, phosphoric acid, hydrochloric acid, ethane sulfonic acid (ESA), or any combination thereof. In some embodiments, the acid is trifluoroacetic acid (TFA).

In some embodiments, $R_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc).

In some embodiments, $R_2$ is $C_{1-10}$ alkyl. In some embodiments, $R_2$ is methyl. In some embodiments, each $R_3$ is H.

In some embodiments, the compound of Formula (9) or salt thereof has a structure of Formula (10):

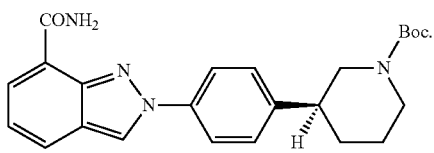
(10)

In some embodiments, the compound of Formula (9) has a structure of Formula (10).

In another aspect, disclosed herein is a process for preparing a salt of Formula (11),

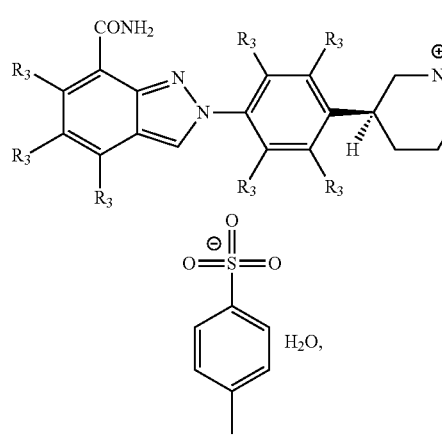
(11)

comprising: contacting a compound of Formula (9),

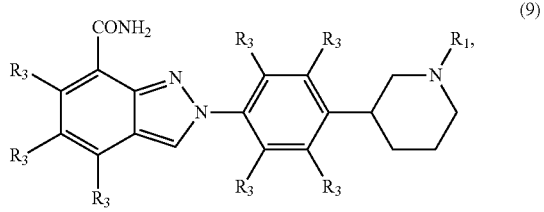

(9)

or a salt thereof, with para-toluene sulfonic acid monohydrate (pTSA.H$_2$O), wherein: R$_1$ is H or an amine protecting group; R$_2$ is H, C$_{1-10}$ alkyl, C$_{1-10}$ haloalkyl, or aryl; and each R$_3$ is independently H, halogen, C$_{1-10}$ alkyl, C$_{1-10}$ haloalkyl, or aryl.

In some embodiments, the contacting is in presence of an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphonic acid, sulfuric acid, nitric acid, phosphoric acid, hydrochloric acid, ethane sulfonic acid (ESA), or any combination thereof. In some embodiments, the acid is trifluoroacetic acid (TFA).

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF.

In some embodiments, R$_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc).

In some embodiments, R$_2$ is C$_{1-10}$ alkyl. In some embodiments, R$_2$ is methyl. In some embodiments, each R$_3$ is H.

In some embodiments, the salt of Formula (11) has a structure of Formula (12):

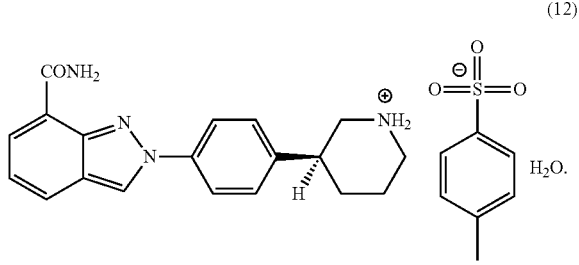

(12)

In another aspect, disclosed herein is a process for preparing an enantiomerically enriched (S)-niraparib tosylate monohydrate of Formula (12),

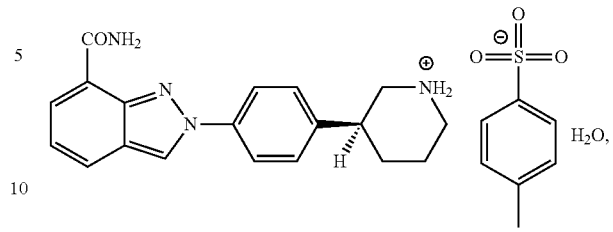

(12)

comprising: contacting a mixture comprising (R)-niraparib tosylate monohydrate and (S)-niraparib tosylate monohydrate with water and a first organic solvent; separating (S)-niraparib tosylate monohydrate from the mixture by filtration to form an enantiomerically enriched (S)-niraparib tosylate monohydrate; and contacting the enantiomerically enriched (S)-niraparib tosylate monohydrate with a second organic solvent, water, or any combination thereof to form a crystalline form of the enantiomerically enriched (S)-niraparib tosylate monohydrate.

In some embodiments, the process further comprising wet milling the crystalline form of the enantiomerically enriched (S)-niraparib tosylate monohydrate. In some embodiments, the process further comprising annealing the enantiomerically enriched (S)-niraparib tosylate monohydrate using one or more temperature cycles.

In some embodiments, the first organic solvent comprises acetonitrile. In some embodiments, a water to first organic solvent ratio (v/v) of from about 200:1 to about 1:200 is used in the contacting. In some embodiments, the water to first organic solvent ratio (v/v) is from about 200:1 to about 1:200, for example, from about 200:1 to about 100:1, from about 200:1 to about 10:1, from about 200:1 to about 5:1, from about 200:1 to about 2:1, from about 200:1 to about 1:1, from about 200:1 to about 1:2, from about 200:1 to about 1:5, from about 200:1 to about 1:10, from about 200:1 to about 1:100, from about 100:1 to about 10:1, from about 100:1 to about 5:1, from about 100:1 to about 2:1, from about 100:1 to about 1:1, from about 100:1 to about 1:2, from about 100:1 to about 1:5, from about 100:1 to about 1:10, from about 100:1 to about 1:100, from about 100:1 to about 1:200, from about 10:1 to about 5:1, from about 10:1 to about 2:1, from about 10:1 to about 1:1, from about 10:1 to about 1:2, from about 10:1 to about 1:5, from about 10:1 to about 1:10, from about 10:1 to about 1:100, from about 10:1 to about 1:200, from about 5:1 to about 2:1, from about 5:1 to about 1:1, from about 5:1 to about 1:2, from about 5:1 to about 1:5, from about 5:1 to about 1:10, from about 5:1 to about 1:100, from about 5:1 to about 1:200, from about 2:1 to about 1:1, from about 2:1 to about 1:2, from about 2:1 to about 1:5, from about 2:1 to about 1:10, from about 2:1 to about 1:100, from about 2:1 to about 1:200, from about 1:1 to about 1:2, from about 1:1 to about 1:5, from about 1:1 to about 1:10, from about 1:1 to about 1:100, from about 1:1 to about 1:200, from about 1:2 to about 1:5, from about 1:2 to about 1:10, from about 1:2 to about 1:100, from about 1:2 to about 1:200, from about 1:5 to about 1:10, from about 1:5 to about 1:100, from about 1:5 to about 1:200, from about 1:10 to about 1:100, from about 1:10 to about 1:200, or from about 1:100 to about 1:200. In some embodiments, the water to first organic solvent ratio (v/v) is from about 5:1 to about 1:5.

In some embodiments, the water to first organic solvent ratio (v/v) is about 1:0.005, about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, about 1:100, about 1:150, or about 1:200.

In some embodiments, the enantiomerically enriched (S)-niraparib tosylate monohydrate is in a filtrate portion (e.g., pass through a filter) after the filtration. In some embodiments, at least about at least about 1% of the enantiomerically enriched (S)-niraparib tosylate monohydrate is in a filtrate portion after the filtration. For example, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the enantiomerically enriched (S)-niraparib tosylate monohydrate is in a filtrate portion after the filtration.

In some embodiments, the second organic solvent comprises DMSO. In some embodiments, the process comprises contacting the enantiomerically enriched (S)-niraparib tosylate monohydrate with dimethyl sulfoxide (DMSO) and water. In some embodiments, a water to second organic solvent ratio (v/v) of from about 200:1 to about 1:200 is used in the contacting. In some embodiments, the water to second organic solvent ratio (v/v) is from about 200:1 to about 1:200, for example, from about 200:1 to about 100:1, from about 200:1 to about 10:1, from about 200:1 to about 5:1, from about 200:1 to about 2:1, from about 200:1 to about 1:1, from about 200:1 to about 1:2, from about 200:1 to about 1:5, from about 200:1 to about 1:10, from about 200:1 to about 1:100, from about 100:1 to about 10:1, from about 100:1 to about 5:1, from about 100:1 to about 2:1, from about 100:1 to about 1:1, from about 100:1 to about 1:2, from about 100:1 to about 1:5, from about 100:1 to about 1:10, from about 100:1 to about 1:100, from about 100:1 to about 1:200, from about 10:1 to about 5:1, from about 10:1 to about 2:1, from about 10:1 to about 1:1, from about 10:1 to about 1:2, from about 10:1 to about 1:5, from about 10:1 to about 1:10, from about 10:1 to about 1:100, from about 10:1 to about 1:200, from about 5:1 to about 2:1, from about 5:1 to about 1:1, from about 5:1 to about 1:2, from about 5:1 to about 1:5, from about 5:1 to about 1:10, from about 5:1 to about 1:100, from about 5:1 to about 1:200, from about 2:1 to about 1:1, from about 2:1 to about 1:2, from about 2:1 to about 1:5, from about 2:1 to about 1:10, from about 2:1 to about 1:100, from about 2:1 to about 1:200, from about 1:1 to about 1:2, from about 1:1 to about 1:5, from about 1:1 to about 1:10, from about 1:1 to about 1:100, from about 1:1 to about 1:200, from about 1:2 to about 1:5, from about 1:2 to about 1:10, from about 1:2 to about 1:100, from about 1:2 to about 1:200, from about 1:5 to about 1:10, from about 1:5 to about 1:100, from about 1:5 to about 1:200, from about 1:10 to about 1:100, from about 1:10 to about 1:200, or from about 1:100 to about 1:200. In some embodiments, the water to second organic solvent ratio (v/v) is from about 5:1 to about 1:5.

In some embodiments, the water to second organic solvent ratio (v/v) is about 1:0.005, about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, about 1:100, about 1:150, or about 1:200.

In some embodiments, the (S)-niraparib tosylate monohydrate and (R)-niraparib tosylate monohydrate, have an enantiomeric excess of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

In another aspect, disclosed herein is a process for preparing an enantiomerically enriched (S)-niraparib tosylate monohydrate of Formula (12),

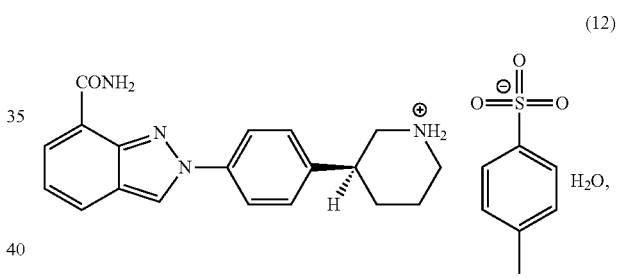

(12)

comprising: contacting a salt of Formula (13),

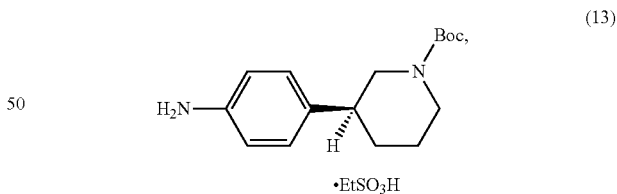

(13)

with sodium hydroxide and toluene, to form a compound of Formula (14),

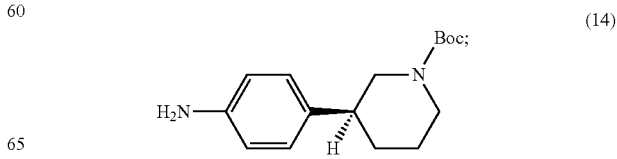

(14)

contacting a compound of Formula (15),

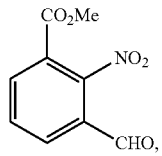 (15)

with sodium azide, ethyl acetate and DMSO, to form a compound of Formula (16),

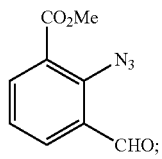 (16)

contacting the compound of Formula (14) with the compound of Formula (16) and TFA, to form a compound of Formula (4),

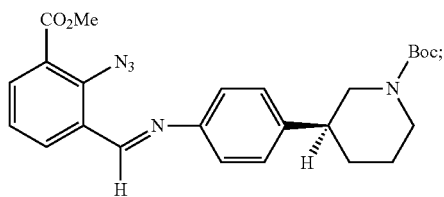 (4)

contacting the compound of Formula (4) with copper(II) trifluoromethanesulfonate (Cu(OTf)$_2$), THF and toluene, to form a compound of Formula (6),

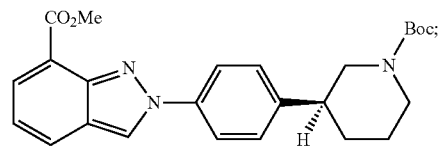 (6)

contacting the compound of Formula (6) with lithium hydroxide and ethanol, to form a salt of Formula (8),

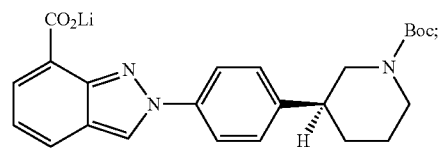 (8)

contacting the salt of Formula (8) with CDI, TFA, N,N-dimethylformide (DMF), and ammonium hydroxide, to form a compound of Formula (10),

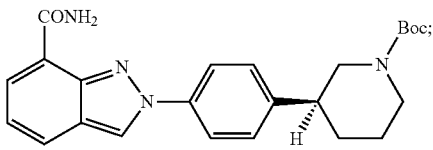 (10)

contacting the compound of Formula (10) with p-Toluenesulfonic acid monohydrate (pTsOH.H$_2$O) and THF, to form (S)-niraparib tosylate monohydrate of Formula (12),

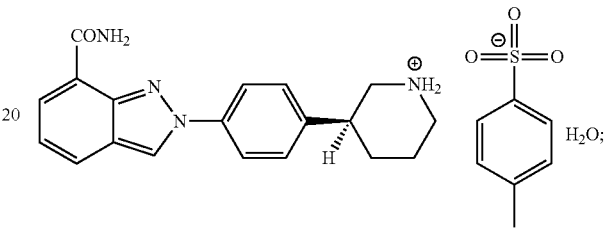 (12)

contacting the (S)-niraparib tosylate monohydrate of Formula (12) with acetonitrile and water, to form a mixture; separating (S)-niraparib tosylate monohydrate from the mixture by filtration, to form an enantiomerically enriched (S)-niraparib tosylate monohydrate; and contacting the enantiomerically enriched (S)-niraparib tosylate monohydrate with DMSO and water, to form a crystalline form of the enantiomerically enriched (S)-niraparib tosylate monohydrate. In some embodiments, the process further comprises wet milling the crystalline form of the enantiomerically enriched (S)-niraparib tosylate monohydrate. In some embodiments, the process further comprises annealing the enantiomerically enriched (S)-niraparib tosylate monohydrate using one or more temperature cycles.

In another aspect, disclosed herein is a salt of Formula (7),

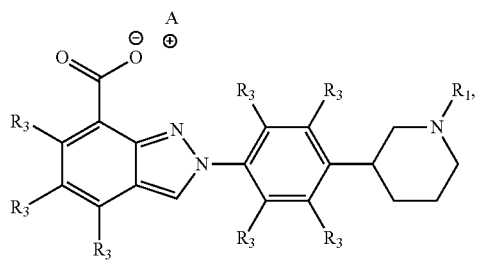 (7)

wherein: $R_1$ is H or an amine protecting group; each $R_3$ is independently H, halogen, $C_{1-10}$ alkyl, $C_{1-10}$ haloalkyl, or aryl; and A is a cation. In some embodiments, the cation is an inorganic or organic cation. In some embodiments, the cation is a metal cation. In some embodiments, the metal cation is an alkali metal cation. In some embodiments, the alkali metal cation is lithium cation. In some embodiments, $R_1$ is an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc). In some embodiments, each $R_3$ is H. In some embodiments, the salt of Formula (7) has a structure of Formula (8):

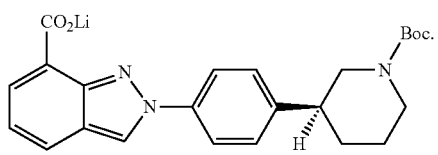
(8)

In another aspect, disclosed herein is a process for preparing a compound of Formula (17),

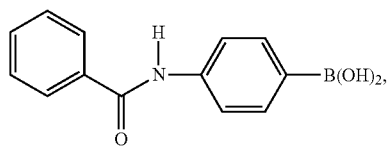
(17)

or a salt thereof, comprising: contacting a compound of Formula (18),

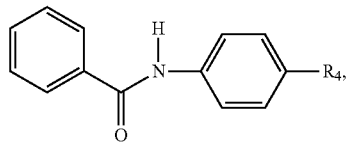
(18)

or a salt thereof, with n-butyl lithium and triisopropyl borate (B(Oi-Pr)$_3$), wherein $R_4$ is a leaving group. In some embodiments, the process further comprises a hydrolysis reaction. In some embodiments, the process comprises contacting a compound of Formula (19),

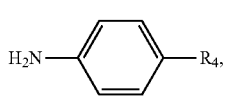
(19)

or a salt thereof, with benzoyl chloride and an organic compound, to form the compound of Formula (18) or salt thereof, wherein $R_4$ is a leaving group. In some embodiments, the organic compound is trimethylamine (TEA) or trimethylamine (TMA). In some embodiments, the leaving group is, for example, dinitrogen, dialkyl ether, perfluoroalkylsulfonate (e.g., triflate), tosylate, mesylate, iodide, bromide, water, alcohol, chloride, nitrate, phosphate, ester, thioether, amine, ammonia, fluoride, carboxylate, phenoxide, hydroxide, alkoxide, or amide. In some embodiments, $R_4$ is Br. In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF.

In another aspect, disclosed herein is a process for preparing a compound of Formula (20),

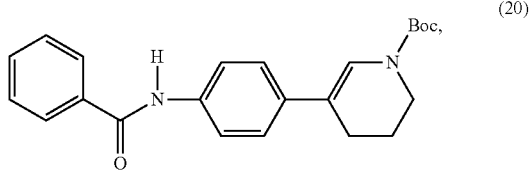 [SMILES: CC(C)(C)OC(=O)N1C=C(c2ccc(NC(=O)c3ccccc3)cc2)CCC1]
(20)

or a salt thereof, comprising: contacting a compound of Formula (17),

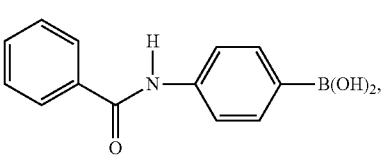
(17)

or a salt thereof, with a salt of Formula (21),

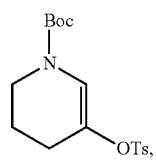
(21)

in presence of a catalyst. In some embodiments, the contacting the compound of Formula (17), or the salt thereof further comprises contacting a salt of Formula (22),

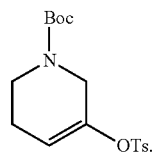
(22)

Also disclosed herein is a process for preparing a compound of Formula (26),

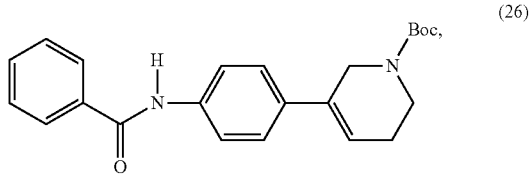
(26)

or a salt thereof, comprising: contacting a compound of Formula (17),

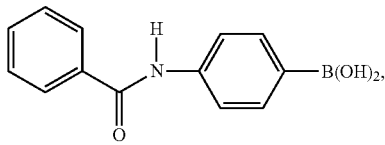 (17)

or a salt thereof, with a salt of Formula (22),

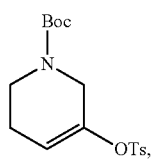 (22)

in presence of a catalyst.

In some embodiments, the salt of Formula (21) and the salt of Formula (22) has a ratio (w/w) of from about 200:1 to about 1:200, for example, from about 200:1 to about 100:1, from about 200:1 to about 10:1, from about 200:1 to about 5:1, from about 200:1 to about 2:1, from about 200:1 to about 1:1, from about 200:1 to about 1:2, from about 200:1 to about 1:5, from about 200:1 to about 1:10, from about 200:1 to about 1:100, from about 100:1 to about 10:1, from about 100:1 to about 5:1, from about 100:1 to about 2:1, from about 100:1 to about 1:1, from about 100:1 to about 1:2, from about 100:1 to about 1:5, from about 100:1 to about 1:10, from about 100:1 to about 1:100, from about 100:1 to about 1:200, from about 10:1 to about 5:1, from about 10:1 to about 2:1, from about 10:1 to about 1:1, from about 10:1 to about 1:2, from about 10:1 to about 1:5, from about 10:1 to about 1:10, from about 10:1 to about 1:100, from about 10:1 to about 1:200, from about 5:1 to about 2:1, from about 5:1 to about 1:1, from about 5:1 to about 1:2, from about 5:1 to about 1:5, from about 5:1 to about 1:10, from about 5:1 to about 1:100, from about 5:1 to about 1:200, from about 2:1 to about 1:1, from about 2:1 to about 1:2, from about 2:1 to about 1:5, from about 2:1 to about 1:10, from about 2:1 to about 1:100, from about 2:1 to about 1:200, from about 1:1 to about 1:2, from about 1:1 to about 1:5, from about 1:1 to about 1:10, from about 1:1 to about 1:100, from about 1:1 to about 1:200, from about 1:2 to about 1:5, from about 1:2 to about 1:10, from about 1:2 to about 1:100, from about 1:2 to about 1:200, from about 1:5 to about 1:10, from about 1:5 to about 1:100, from about 1:5 to about 1:200, from about 1:10 to about 1:100, from about 1:10 to about 1:200, or from about 1:100 to about 1:200. In some embodiments, the salt of Formula (21) and the salt of Formula (22) has a ratio (w/w) of from about 10:1 to about 1:1.

In some embodiments, the salt of Formula (21) and the salt of Formula (22) has a ratio (w/w) of about 1:0.005, about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, about 1:100, about 1:150, or about 1:200. In some embodiments, the salt of Formula (21) and the salt of Formula (22) has a ratio (w/w) of about 7:1. In some embodiments, the salt of Formula (21) and the salt of Formula (22) has a ratio (w/w) of about 9:1.

In some embodiments, the contacting is in presence of a ligand. In some embodiments, the ligand comprises a phosphine ligand. In some embodiments, the phosphine ligand comprises DavePhos, XantPhos, JohnPhos, SPhos, XPhos, tBuXPhos, APhos, CyJohnPhos, or any combination thereof. In some embodiments, the phosphine ligand comprises XPhos. In some embodiments, the phosphine ligand can be optically enriched. In some embodiments, the phosphine ligand can be optically enriched before being used in the processes and methods disclosed herein. In some embodiments, the phosphine ligand (e.g., optically enriched phosphine ligand) have an enantiomeric excess of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

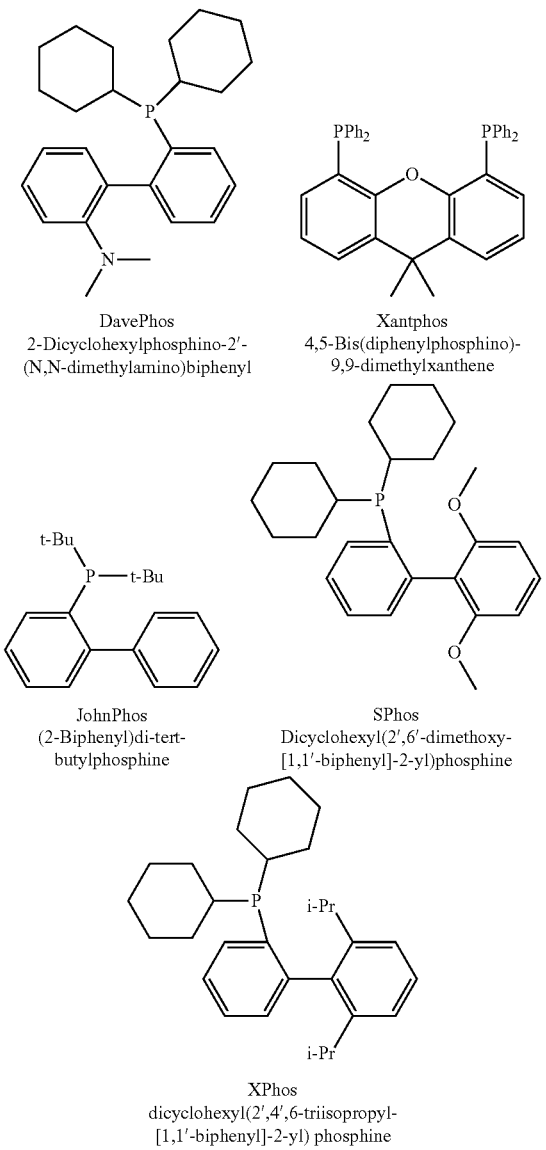

DavePhos
2-Dicyclohexylphosphino-2'-
(N,N-dimethylamino)biphenyl

Xantphos
4,5-Bis(diphenylphosphino)-
9,9-dimethylxanthene

JohnPhos
(2-Biphenyl)di-tert-
butylphosphine

SPhos
Dicyclohexyl(2',6'-dimethoxy-
[1,1'-biphenyl]-2-yl)phosphine

XPhos
dicyclohexyl(2',4',6-triisopropyl-
[1,1'-biphenyl]-2-yl) phosphine

-continued

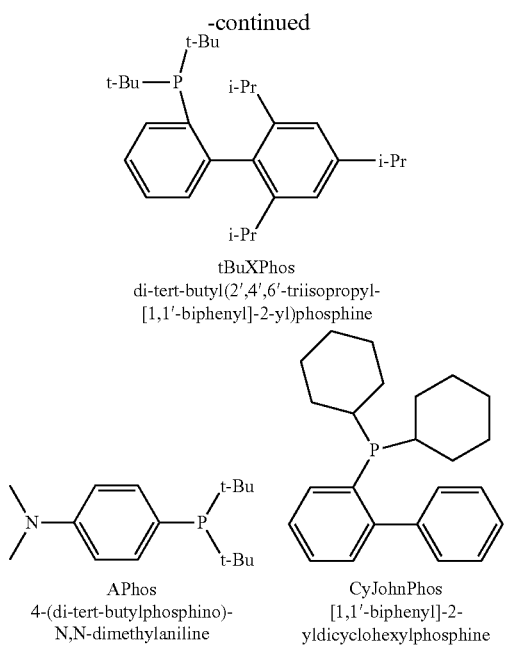

tBuXPhos
di-tert-butyl(2',4',6'-triisopropyl-
[1,1'-biphenyl]-2-yl)phosphine

APhos
4-(di-tert-butylphosphino)-
N,N-dimethylaniline

CyJohnPhos
[1,1'-biphenyl]-2-
yldicyclohexylphosphine

In some embodiments, the catalyst comprises a metal catalyst. In some embodiments, the metal catalyst comprises a transition metal catalyst. In some embodiments, the metal catalyst comprises scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, ununnilium, unununium, or ununbium. In some embodiments, the metal catalyst comprises palladium. In some embodiments, the metal catalyst comprises palladium(II) acetate.

In some embodiments, the contacting is in presence of a base. In some embodiments, the base comprises an alkali salt. In some embodiments, the alkali salt comprises $Cs_2CO_3$, $CsHCO_3$ $K_3PO_4$, $K_2HPO_4$, $KH_2PO_4$, $K_2CO_3$, $KHCO_3$, $NaHCO_3$, $Na_2CO_3$, or any combination thereof.

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF. In some embodiments, the process further comprises contacting the compound of Formula (20) or salt thereof, with acetonitrile.

In another aspect, disclosed herein is a process for preparing a compound of Formula (23),

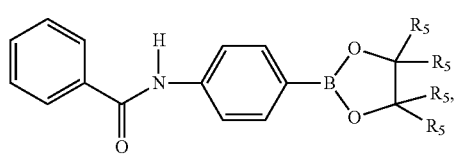

or a salt thereof, comprising: contacting a compound of Formula (17),

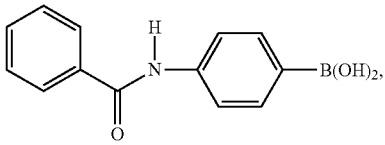

or a salt thereof, with

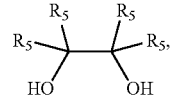

wherein each $R_5$ is independently H or $C_{1-3}$ alkyl. In some embodiments, each $R_5$ is independently $C_{1-3}$ alkyl. In some embodiments, each $R_5$ is methyl. In some embodiments, the compound of Formula (23) or salt thereof has a structure of Formula (24),

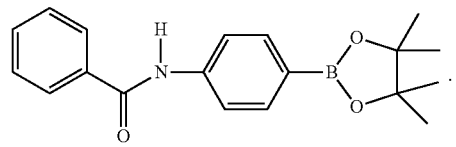

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF.

In another aspect, disclosed herein is a process for preparing a compound of Formula (20),

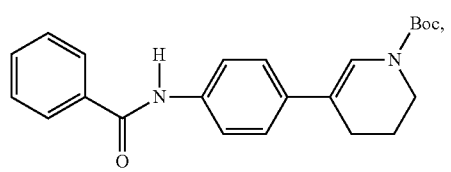

or a salt thereof, comprising: contacting the compound of Formula (23),

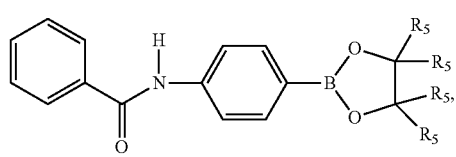

or the salt thereof, with a salt of Formula (21)

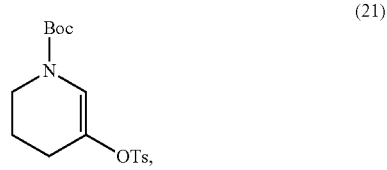 [SMILES: Cc1ccc(S(=O)(=O)OC2=CN(C(=O)OC(C)(C)C)CCC2)cc1]

in the presence of a catalyst. Also disclosed herein is a process for preparing a compound of Formula (26),

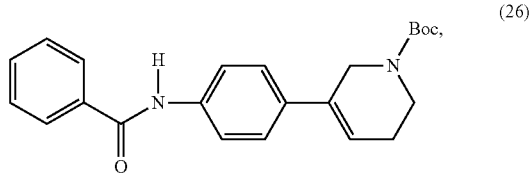 [SMILES: CC(C)(C)OC(=O)N1CCC=C(c2ccc(NC(=O)c3ccccc3)cc2)C1]

or a salt thereof, comprising: contacting the compound of Formula (23),

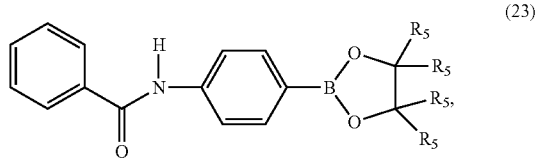

or the salt thereof, with a salt of Formula (22),

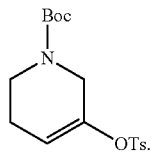 [SMILES: Cc1ccc(S(=O)(=O)OC2=CCCN(C(=O)OC(C)(C)C)C2)cc1]

In some embodiments, the salt of Formula (21) and the salt of Formula (22) has a ratio (w/w) of from about 200:1 to about 1:200, for example, from about 200:1 to about 100:1, from about 200:1 to about 10:1, from about 200:1 to about 5:1, from about 200:1 to about 2:1, from about 200:1 to about 1:1, from about 200:1 to about 1:2, from about 200:1 to about 1:5, from about 200:1 to about 1:10, from about 200:1 to about 1:100, from about 100:1 to about 10:1, from about 100:1 to about 5:1, from about 100:1 to about 2:1, from about 100:1 to about 1:1, from about 100:1 to about 1:2, from about 100:1 to about 1:5, from about 100:1 to about 1:10, from about 100:1 to about 1:100, from about 100:1 to about 1:200, from about 10:1 to about 5:1, from about 10:1 to about 2:1, from about 10:1 to about 1:1, from about 10:1 to about 1:2, from about 10:1 to about 1:5, from about 10:1 to about 1:10, from about 10:1 to about 1:100, from about 10:1 to about 1:200, from about 5:1 to about 2:1, from about 5:1 to about 1:1, from about 5:1 to about 1:2, from about 5:1 to about 1:5, from about 5:1 to about 1:10, from about 5:1 to about 1:100, from about 5:1 to about 1:200, from about 2:1 to about 1:1, from about 2:1 to about 1:2, from about 2:1 to about 1:5, from about 2:1 to about 1:10, from about 2:1 to about 1:100, from about 2:1 to about 1:200, from about 1:1 to about 1:2, from about 1:1 to about 1:5, from about 1:1 to about 1:10, from about 1:1 to about 1:100, from about 1:1 to about 1:200, from about 1:2 to about 1:5, from about 1:2 to about 1:10, from about 1:2 to about 1:100, from about 1:2 to about 1:200, from about 1:5 to about 1:10, from about 1:5 to about 1:100, from about 1:5 to about 1:200, from about 1:10 to about 1:100, from about 1:10 to about 1:200, or from about 1:100 to about 1:200. In some embodiments, the salt of Formula (21) and the salt of Formula (22) has a ratio (w/w) of from about 10:1 to about 1:1.

In some embodiments, the salt of Formula (21) and the salt of Formula (22) has a ratio (w/w) of about 1:0.005, about 1:0.01, about 1:0.02, about 1:0.03, about 1:0.04, about 1:0.05, about 1:0.1, about 1:0.2, about 1:0.3, about 1:0.4, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:20, about 1:30, about 1:40, about 1:50, about 1:60, about 1:70, about 1:80, about 1:90, about 1:100, about 1:150, or about 1:200. In some embodiments, the salt of Formula (21) and the salt of Formula (22) has a ratio (w/w) of about 7:1. In some embodiments, the salt of Formula (21) and the salt of Formula (22) has a ratio (w/w) of about 9:1.

In some embodiments, the contacting is in presence of a ligand. In some embodiments, the ligand comprises a phosphine ligand. In some embodiments, the phosphine ligand comprises DavePhos, XantPhos, JohnPhos, SPhos, XPhos, tBuXPhos, APhos, CyJohnPhos, or any combination thereof. In some embodiments, the phosphine ligand comprises XPhos.

In some embodiments, the catalyst comprises a metal catalyst. In some embodiments, the metal catalyst comprises a transition metal catalyst. In some embodiments, the metal catalyst comprises scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, ununnilium, unununium, or ununbium. In some embodiments, the metal catalyst comprises palladium. In some embodiments, the metal catalyst comprises palladium(II) acetate.

In some embodiments, the contacting is in presence of a base. In some embodiments, the base comprises an alkali salt. In some embodiments, the alkali salt comprises $Cs_2CO_3$, $CsHCO_3 K_3PO_4$, $K_2HPO_4$, $KH_2PO_4$, $K_2CO_3$, $KHCO_3$, $NaHCO_3$, $Na_2CO_3$, or any combination thereof.

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF. In some embodiments, the process further comprises contacting the compound of Formula (20) or salt thereof, with acetonitrile.

In another aspect, disclosed herein is a process for preparing a compound of Formula (25),

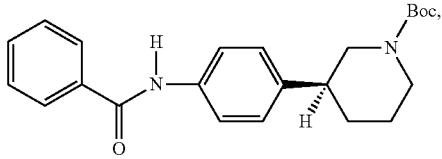

(25)

or a salt thereof, comprising: contacting a compound of Formula (20),

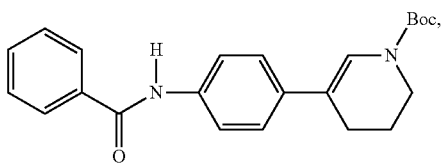

(20)

or a salt thereof, with a ligand. In some embodiments, the process further comprises contacting a compound of Formula (26),

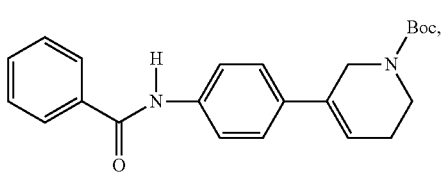

(26)

or a salt thereof, with the ligand.

In some embodiments, the ligand comprises a chiral ligand. In some embodiments, the chiral ligand comprises a Josiphos ligand. In some embodiments, the Josiphos ligand comprises Josiphos SL-J505-2, Josiphos SL-J013, Josiphos SL-J212, Josiphos SL-J011, Josiphos SL-N012, or any combination thereof. In some embodiments, the contacting is in presence of a metal salt. In some embodiments, the metal salt comprises rhodium. In some embodiments, the metal salt comprises rhodium(I). In some embodiments, the metal salt comprises bis(norbornadiene)rhodium(I) tetrafluoroborate (Rh(nbd)$_2$BF$_4$). In some embodiments, the ligand can be optically enriched. In some embodiments, the ligand can be optically enriched before being used in the processes and methods disclosed herein. In some embodiments, the ligand (e.g., optically enriched ligand) have an enantiomeric excess of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

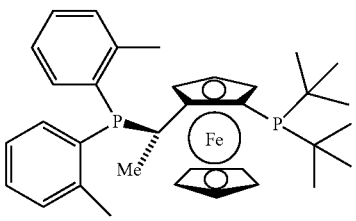

Josiphos-SL-J505-2

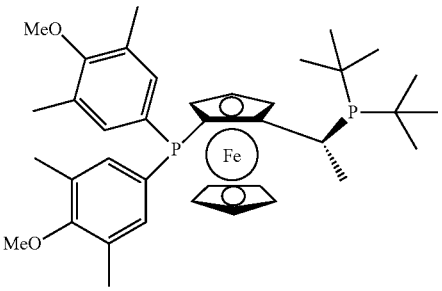

Josiphos-SL-J013

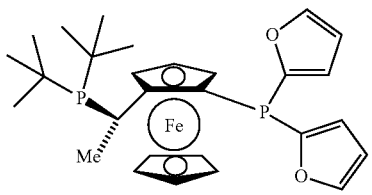

Josiphos-SL-J212

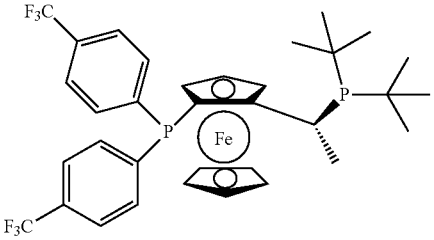

Josiphos-SL-J011

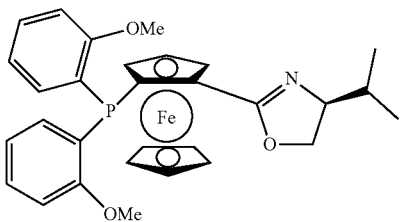

Josiphos-SL-N012

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises DCM.

In another aspect, disclosed herein is a process for preparing a compound of Formula (14),

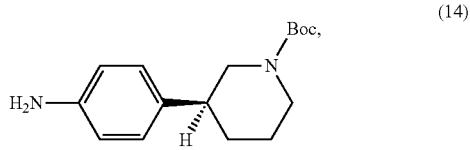 [SMILES: CC(C)(C)OC(=O)N1CCC[C@@H](c2ccc(N)cc2)C1]

(14)

or a salt thereof, comprising: contacting a compound of Formula (25),

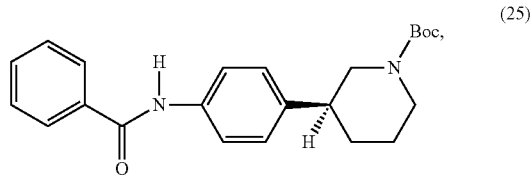 [SMILES: CC(C)(C)OC(=O)N1CCC[C@@H](c2ccc(NC(=O)c3ccccc3)cc2)C1]

(25)

or a salt thereof, with a base. In some embodiments, the base comprises an alkali hydroxide. In some embodiments, the alkali hydroxide is lithium hydroxide (LiOH), sodium hydroxide (NaOH), potassium hydroxide (KOH), rubidium hydroxide (RbOH), or caesium hydroxide (CsOH). In some embodiments, the alkali hydroxide comprises sodium hydroxide.

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises ethanol.

In another aspect, disclosed herein is a process for preparing a salt of Formula (13),

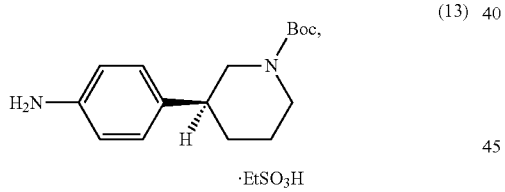

(13)

comprising: contacting a compound of Formula (14),

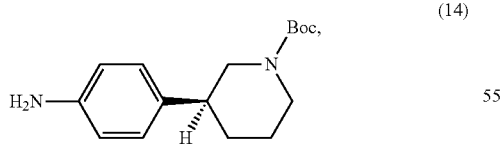

(14)

or a salt thereof, with an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphoric acid, sulfuric acid, nitric acid, phosphoric acid, hydrochloric acid, ethane sulfonic acid (ESA), or any combination thereof. In some embodiments, the acid is ESA.

In some embodiments, the contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises acetonitrile, methanol, DCM, or any combination thereof. In some embodiments, the solvent comprises acetonitrile and methanol.

In some embodiments, the solvent has a methanol to acetonitrile ratio of about 0.1% to 99% (v/v). For example, the methanol to acetonitrile ratio (v/v) is about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, or about 95%-99%. In some embodiments, the methanol to acetonitrile ratio (v/v) is about 1%-50%.

In some embodiments, the solvent comprises acetonitrile and DCM. For example, the DCM to acetonitrile ratio (v/v) is about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, or about 95%-99%. In some embodiments, the DCM to acetonitrile ratio (v/v) is about 1%-50%.

In some embodiments, the compound of Formula (14),

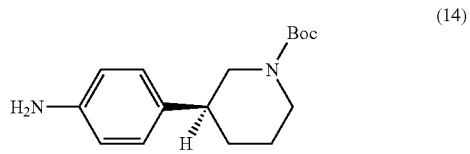 [SMILES: CC(C)(C)OC(=O)N1CCC[C@@H](c2ccc(N)cc2)C1]

(14)

or salt thereof, and a compound of Formula (27),

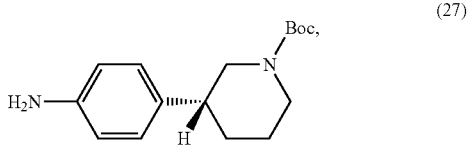 [SMILES: CC(C)(C)OC(=O)N1CCC[C@H](c2ccc(N)cc2)C1]

(27)

or salt thereof, have an enantiomeric excess of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

In another aspect, disclosed herein is a process for preparing a compound of Formula (21),

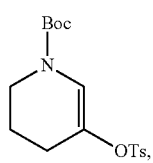

(21)

or a salt thereof, comprising: oxidizing a compound of Formula (28),

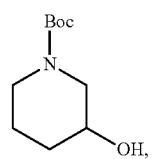

(28)

or a salt thereof, to form a compound of Formula (29),

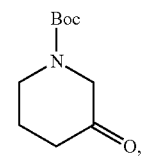

(29)

or a salt thereof; and contacting the compound of Formula (29) or salt thereof, with p-Toluenesulfonic anhydride. In some embodiments, the oxidizing is in presence of an oxidizing agent. In some embodiments, the oxidizing is in presence of 2,2,6,6-tetramethylpiperidine-1-oxyl (TEMPO).

In some embodiments, the oxidizing or contacting is in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises DCM.

In some embodiments, the oxidizing the compound of Formula (28),

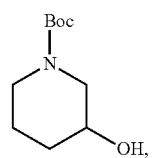

(28)

or salt thereof, is in presence of sodium bicarbonate, potassium bromide, sodium sulfite, or any combination thereof. In some embodiments, the contacting the compound of Formula (29) or salt thereof is in presence of trimethylamine (TEA), water, isopropyl alcohol, sodium azide, or any combination thereof.

In some embodiments, the contacting the compound of Formula (29) or salt thereof results in formation of a mixture of the compound of Formula (21),

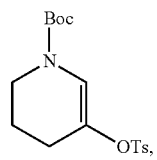

(21)

and the compound of Formula (22),

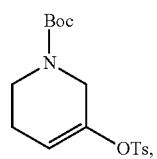

(22)

In another aspect, disclosed herein is a composition of Formula (30),

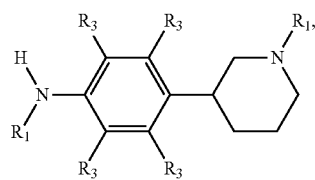

(30)

or a salt thereof, wherein: each $R_1$ is independently H or an amine protecting group; and each $R_3$ is independently H, halogen, $C_{1-10}$ alkyl, $C_{1-10}$ haloalkyl, or aryl.

In some embodiments, each $R_1$ is independently an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc) or benzoyl (Bz). In some embodiments, each $R_3$ is H.

In another aspect, disclosed herein is a composition of Formula (31) or (32),

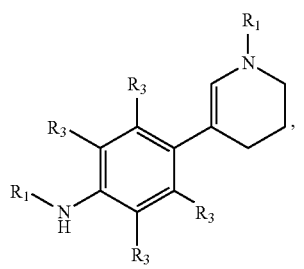

(31)

-continued

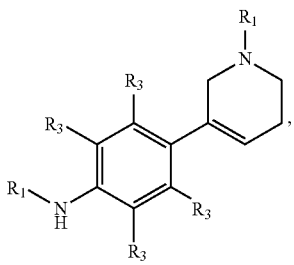
(32)

or a salt thereof, wherein: each $R_1$ is independently H or an amine protecting group; and each $R_3$ is independently H, halogen, $C_{1-10}$ alkyl, $C_{1-10}$ haloalkyl, or aryl.

In some embodiments, each $R_1$ is independently an amine protecting group. In some embodiments, the amine protecting group is tert-butyloxycarbonyl (Boc), 9-fluorenylmethyloxycarbonyl (Fmoc), carboxybenzyl group (Cbz), p-methoxybenzyl carbonyl (Moz), acetyl (Ac), benzoyl (Bz), p-methoxybenzyl (PMB), 3,4-dimethoxybenzyl (DMPM), p-methoxyphenyl (PMP), 2-naphthylmethyl ether (Nap), tosyl (Ts), or trichloroethyl chloroformate (Troc). In some embodiments, the amine protecting group is tert-butyloxycarbonyl group (Boc) or benzoyl (Bz). In some embodiments, each $R_3$ is H.

In some embodiments, the compound or salt thereof has a structure of Formula (20):

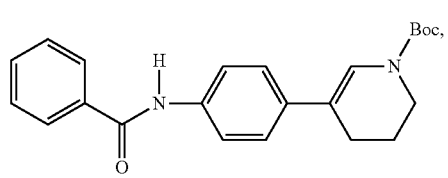
(20)

or Formula (26):

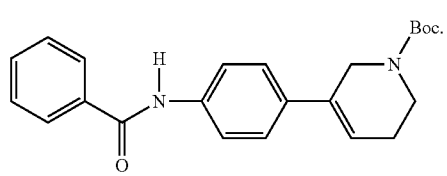
(26)

In some embodiments, the compound or salt thereof has a structure of Formula (20). In some embodiments, the compound or salt thereof has a structure of Formula (20).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
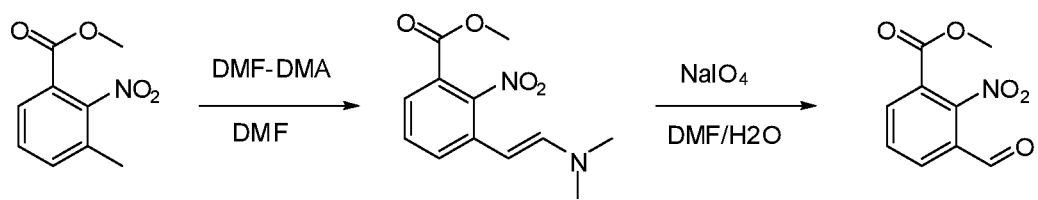
FIG. 1 shows the synthesis of the compound methyl 3-formyl-2-nitrobenzoate (Aldehyde A).

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

As used in the specification and appended claims, unless specified to the contrary, the following terms have the meaning indicated below.

The compounds disclosed herein may contain one or more asymmetric centers and may thus give rise to enantiomers, diastereomers, and other stereoisomeric forms that may be defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

"Enantiomeric excess (ee)" refers the degree to which a sample contains one enantiomer in greater amounts than the other. For example, a racemic mixture has an ee of 0%, while a single completely pure enantiomer has an ee of 100%. In another example, a sample with 70% of one enantiomer and 30% of the other has an ee of 40% (70%-30%). For instance, if there are two enantiomers and their mole or weight percentages are R and S, then ee can be calculated as: ee=[(R−S)/(R+S)]*100%. For example, a racemic mixture (R=S=50%) has an ee of 0%, while a single completely pure enantiomer has an ee of 100%. In another example, a sample with 70% of one enantiomer and 30% of the other has an ee of 40% (70%-30%). In some embodiments, the enantiomers disclosed herein have an enantiomeric excess of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%.

"Amino" refers to the —NH$_2$ radical.

"Alkyl" refers to a straight or branched hydrocarbon chain radical consisting solely of carbon and hydrogen atoms, containing no unsaturation, having from one to fifteen carbon atoms (e.g., C$_{1-15}$ alkyl). In certain embodiments, an alkyl comprises one to thirteen carbon atoms (e.g., C$_{1-13}$ alkyl). In certain embodiments, an alkyl comprises one to ten carbon atoms (e.g., C$_{1-10}$ alkyl). In certain embodiments, an alkyl comprises one to eight carbon atoms (e.g., C$_{1-8}$ alkyl). In other embodiments, an alkyl comprises one to five carbon atoms (e.g., C$_{1-5}$ alkyl). In other embodiments, an alkyl comprises one to four carbon atoms (e.g., C$_{1-4}$ alkyl). In other embodiments, an alkyl comprises one to three carbon atoms (e.g., C$_{1-3}$ alkyl). In other embodiments, an alkyl comprises one to two carbon atoms (e.g., C$_{1-2}$ alkyl). In other embodiments, an alkyl comprises one carbon atom (e.g., C$_1$ alkyl). In other embodiments, an alkyl comprises five to fifteen carbon atoms (e.g., C$_{5-15}$ alkyl). In other embodiments, an alkyl comprises five to ten carbon atoms (e.g., C$_{5-10}$ alkyl). In other embodiments, an alkyl comprises five to eight carbon atoms (e.g., C$_{5-8}$ alkyl). In other embodiments, an alkyl comprises two to five carbon atoms (e.g., C$_{2-5}$ alkyl). In other embodiments, an alkyl comprises three to five carbon atoms (e.g., C$_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$) C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_{1-8}$ alkylene). In other embodiments, an alkylene comprises one to five carbon atoms (e.g., $C_{1-5}$ alkylene). In other embodiments, an alkylene comprises one to four carbon atoms (e.g., $C_{1-4}$ alkylene). In other embodiments, an alkylene comprises one to three carbon atoms (e.g., $C_{1-3}$ alkylene). In other embodiments, an alkylene comprises one to two carbon atoms (e.g., $C_{1-2}$ alkylene). In other embodiments, an alkylene comprises one carbon atom (e.g., $C_1$ alkylene). In other embodiments, an alkylene comprises five to eight carbon atoms (e.g., $C_{5-8}$ alkylene). In other embodiments, an alkylene comprises two to five carbon atoms (e.g., $C_{2-5}$ alkylene). In other embodiments, an alkylene comprises three to five carbon atoms (e.g., $C_{3-5}$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aralkyl" refers to a radical of the formula —R$_c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]

heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)OR$^a$, —$R^b$—OC(O)—N($R^a$)$_2$, —$R^b$—N($R^a$)$_2$, —$R^b$—C(O)R$^a$, —$R^b$—C(O)OR$^a$, —$R^b$—C(O)N($R^a$)$_2$, —$R^b$—O—$R^c$—C(O)N($R^a$)$_2$, —$R^b$—N($R^a$)C(O)OR$^a$, —$R^b$—N($R^a$)C(O)R$^a$, —$R^b$—N($R^a$)S(O)$_t$R$^a$ (where t is 1 or 2), —$R^b$—S(O)$_t$R$^a$ (where t is 1 or 2), —$R^b$—S(O)$_t$OR$^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo" or "halogen" refers to bromo, chloro, fluoro or iodo substituents.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—OR$^a$, —$R^b$—OC(O)—N($R^a$)$_2$, —$R^b$—N($R^a$)$_2$, —$R^b$—C(O)R$^a$, —$R^b$—C(O)OR$^a$, —$R^b$—C(O)N($R^a$)$_2$, —$R^b$—O—$R^c$—C(O)N($R^a$)$_2$, —$R^b$—N($R^a$)C(O)OR$^a$, —$R^b$—N($R^a$)C(O)R$^a$, —$R^b$—N($R^a$)S(O)$_t$R$^a$ (where t is 1 or 2), —$R^b$—S(O)$_t$R$^a$ (where t is 1 or 2), —$R^b$—S(O)$_t$OR$^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

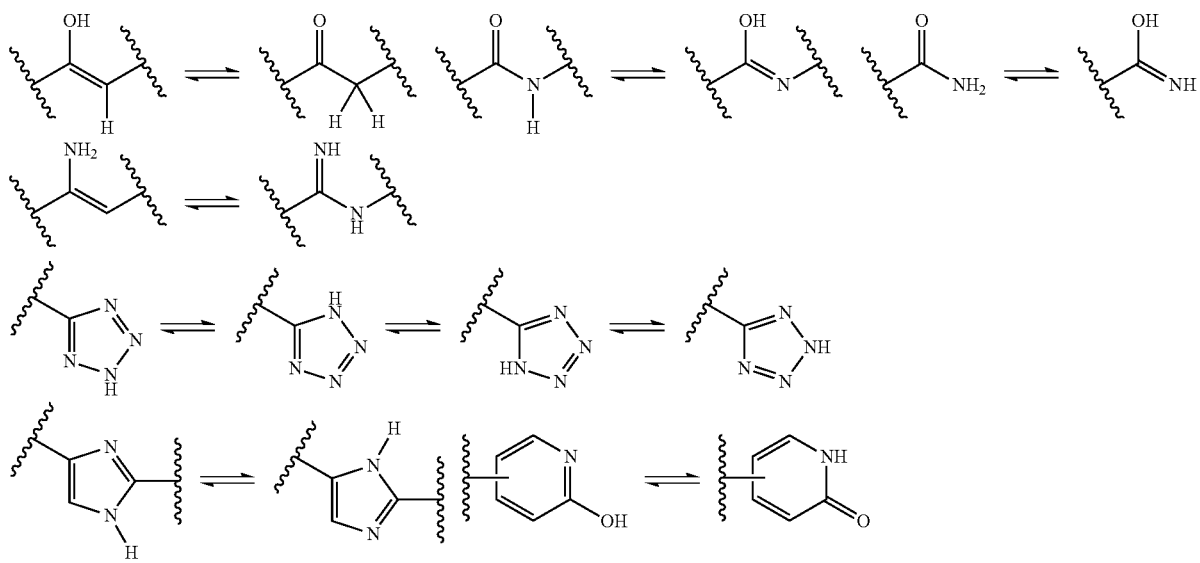

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods.

"Leaving group" is defined as a term that would be understood by one of ordinary skill in the art; that is, a group on a carbon where, upon reaction, a new bond is to be formed and the carbon loses the group upon formation of the new bond. A typical example employing a suitable leaving group is a nucleophilic substitution reaction, e.g., on a sp$^3$ hybridized carbon (S$_N$2 or S$_N$1), e.g., where the leaving group is a halide, such as a bromide, and the reactant might be benzyl bromide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Leaving group" is not limited to such mechanistic restrictions. Examples of suitable leaving groups include halogens (fluorine, chlorine, bromine or iodine), optionally substituted aryl or alkyl sulfonates, phosphonates, azides and —S(O)$_{0-2}$R where R is, for example, optionally substituted alkyl, optionally substituted aryl, or optionally substituted heteroaryl. Those of skill in the art of organic synthesis will readily identify suitable leaving groups to perform a desired reaction under different reaction conditions. Non-limiting characteristics and examples of leaving groups can be found, for example in Organic Chemistry, 2nd ed., Francis Carey (1992), pages 328-331; Introduction to Organic Chemistry, 2d ed., Andrew Streitwieser and Clayton Heathcock (1981), pages 169-171; and Organic Chemistry, 5th Ed., John McMurry, Brooks/Cole Publishing (2000), pages 398 and 408; all of which are incorporated herein by reference.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," 4th Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amine protecting groups include, but are not limited to, formyl, acetyl (Ac), trifluoroacetyl, benzyl (Bn), benzoyl (Bz), carbamate, benzyloxycarbonyl ("CBZ"), p-methoxybenzyl carbonyl (Moz or MeOZ), tertbutoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), p-methoxybenzyl (PMB), tosyl (Ts) and the like.

"Solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

"Salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

"Solvent" can include, but is not limited to, non-polar, polar aprotic, and polar protic solvents. Illustrative examples of non-polar solvents include, but are not limited to, pentane, cyclopentane, hexane, cyclohexane, benzene, toluene, 1,4-dioxane, chloroform, diethyl ether, and dichloromethane (DCM). Illustrative examples of polar aprotic solvents include, but are not limited to, tetrahydrofuran (THF), ethyl acetate, acetone, dimethylformamide (DMF), acetonitrile (MeCN), dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water.

"Transition metal" can include, but is not limited to, scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, ununnilium, unununium, and ununbium.

"Acid" refers to molecules or ions capable of donating a hydron (proton or hydrogen ion H+), or, alternatively, capable of forming a covalent bond with an electron pair (e.g., a Lewis acid). Acids can include, but are not limited to, mineral acids, sulfonic acids, carboxylic acids, halogenated carboxylic acids, vinylogous carboxylic acids, and nucleic acids. Illustrative examples of mineral acids include, but are not limited to, hydrogen halides and their solutions: hydrofluoric acid (HF), hydrochloric acid (HCl), hydrobromic acid (HBr), hydroiodic acid (HI); halogen oxoacids: hypochlorous acid (HClO), chlorous acid ($HClO_2$), chloric acid ($HClO_3$), perchloric acid ($HClO_4$), and corresponding analogs for bromine and iodine, and hypofluorous acid (HFO); sulfuric acid ($H_2SO_4$); fluorosulfuric acid ($HSO_3F$); nitric acid ($HNO_3$); phosphoric acid ($H_3PO_4$); fluoroantimonic acid ($HSbF_6$); fluoroboric acid ($HBF_4$); hexafluorophosphoric acid ($HPF_6$); chromic acid ($H_2CrO_4$); and boric acid ($H_3BO_3$). Illustrative examples of sulfonic acids include, but are not limited to, methanesulfonic acid (or mesylic acid, $CH_3SO_3H$), ethanesulfonic acid (or esylic acid, $CH_3CH_2SO_3H$), benzenesulfonic acid (or besylic acid, $C_6H_5SO_3H$), p-toluenesulfonic acid (or tosylic acid, $CH_3C_6H_4SO_3H$), trifluoromethanesulfonic acid (or triflic acid, $CF_3SO_3H$), and polystyrene sulfonic acid (sulfonated polystyrene, $[CH_2CH(C_6H_4)SO_3H]_n$). Illustrative examples of carboxylic acids include, but are not limited to, acetic acid ($CH_3COOH$), citric acid ($C_6H_8O_7$), formic acid (HCOOH), gluconic acid ($HOCH_2$—$(CHOH)_4$—COOH), lactic acid ($CH_3$—CHOH—COOH), oxalic acid (HOOC—COOH), and tartaric acid (HOOC—CHOH—CHOH—COOH). Illustrative examples of halogenated carboxylic acids include, but are not limited to, fluoroacetic acid, trifluoroacetic acid, chloroacetic acid, dichloroacetic acid, and trichloroacetic acid. Illustrative examples of vinylogous carboxylic acids include, but are not limited to, ascorbic acid. Illustrative examples of nucleic acids include, but are not limited to, deoxyribonucleic acid (DNA) and ribonucleic acid (RNA).

"Base" refers to molecules or ions capable of accepting protons from a proton donor and/or produce hydroxide ions ($OH^-$). Illustrative examples of bases include, but are not limited to, aluminum hydroxide ($Al(OH)_3$), ammonium hydroxide ($NH_4OH$), arsenic hydroxide ($As(OH)_3$), barium hydroxide ($Ba(OH)_2$), beryllium hydroxide ($Be(OH)_2$), bismuth(III) hydroxide ($Bi(OH)_3$), boron hydroxide ($B(OH)3$), cadmium hydroxide ($Cd(OH)_2$), calcium hydroxide ($Ca(OH)_2$), cerium(III) hydroxide ($Ce(OH)_3$), cesium hydroxide (CsOH), chromium(II) hydroxide ($Cr(OH)_2$), chromium(III) hydroxide ($Cr(OH)_3$), chromium(V) hydroxide ($Cr(OH)_5$), chromium(VI) hydroxide ($Cr(OH)_6$), cobalt(II) hydroxide ($Co(OH)_2$), cobalt(III) hydroxide ($Co(OH)_3$), copper(I) hydroxide (CuOH), copper(II) hydroxide ($Cu(OH)_2$), gallium(II) hydroxide ($Ga(OH)_2$), gallium(III) hydroxide ($Ga(OH)_3$), gold(I) hydroxide (AuOH), gold(III) hydroxide ($Au(OH)_3$), indium(I) hydroxide (InOH), indium(II) hydroxide ($In(OH)_2$), indium(III) hydroxide ($In(OH)_3$), iridium(III) hydroxide ($Ir(OH)_3$), iron(II) hydroxide ($Fe(OH)_2$), iron(III) hydroxide ($Fe(OH)_3$), lanthanum hydroxide (La(OH), lead (II) hydroxide ($Pb(OH)_2$), lead(IV) hydroxide ($Pb(OH)_4$), lithium hydroxide (LiOH), magnesium hydroxide ($Mg(OH)_2$), manganese(II) hydroxide ($Mn(OH)_2$), manganese(III) hydroxide ($Mn(OH)_3$), manganese(IV) hydroxide ($Mn(OH)_4$), manganese(VII) hydroxide ($Mn(OH)_7$), mercury(I) hydroxide ($Hg_2(OH)_2$), mercury(II) hydroxide ($Hg(OH)_2$), molybdenum hydroxide ($Mo(OH)_3$), neodymium hydroxide ($Nd(OH)_3$), nickel oxo-hydroxide (NiOOH), nickel(II) hydroxide ($Ni(OH)_2$), nickel(III) hydroxide ($Ni(OH)_3$), niobium hydroxide ($Nb(OH)_3$), osmium(IV) hydroxide ($Os(OH)_4$), palladium(II) hydroxide ($Pd(OH)_2$), palladium(IV) hydroxide ($Pd(OH)_4$), platinum(II) hydroxide ($Pt(OH)_2$), platinum(IV) hydroxide ($Pt(OH)_4$), plutonium (IV) hydroxide ($Pu(OH)_4$), potassium hydroxide (KOH), radium hydroxide ($Ra(OH)_2$), rubidium hydroxide (RbOH), ruthenium(III) hydroxide ($Ru(OH)_3$), scandium hydroxide ($Sc(OH)_3$), silicon hydroxide ($Si(OH)_4$), silver hydroxide (AgOH), sodium hydroxide (NaOH), strontium hydroxide ($Sr(OH)_2$), tantalum(V) hydroxide ($Ta(OH)_5$), technetium (II) hydroxide ($Tc(OH)_2$), tetramethylammonium hydroxide ($C_4H_{12}NOH$), thallium(I) hydroxide (TlOH), thallium(III) hydroxide ($Tl(OH)_3$), thorium hydroxide ($Th(OH)_4$), tin(II) hydroxide ($Sn(OH)_2$), tin(IV) hydroxide ($Sn(OH)_4$), titanium(II) hydroxide ($Ti(OH)_2$), titanium(III) hydroxide ($Ti(OH)_3$), titanium(IV) hydroxide ($Ti(OH)_4$), tungsten(II) hydroxide ($W(OH)_2$), uranyl hydroxide (($UO_2)_2(OH)_4$), vanadium(II) hydroxide ($V(OH)_2$), vanadium(III) hydroxide ($V(OH)_3$), vanadium(V) hydroxide ($V(OH)_5$), ytterbium hydroxide (Yb(OH)$_3$), yttrium hydroxide (Y(OH)$_3$), zinc hydroxide (Zn(OH)$_2$), and zirconium hydroxide (Zr(OH)$_4$).

In certain embodiments, the processes disclosed herein can take place concurrently, in a sequential order as described herein, or in any possible order thereof.

In certain embodiments of the process, the temperature of the disclosed reactions can be chosen to maximize the reaction rate at higher temperatures while maintaining the activity of the reaction for efficient synthesis. In certain embodiments, a reaction is conducted at a temperature of about 5-150° C., for example, about 5-150° C., about 5-130° C., about 5-110° C., about 5-90° C., about 5-70° C., about 5-50° C., about 5-30° C., about 5-10° C., about 10-150° C., about 10-130° C., about 10-110° C., about 10-90° C., about 10-70° C., about 10-50° C., about 10-30° C., about 30-150° C., about 30-130° C., about 30-110° C., about 30-90° C., about 30-70° C., about 30-50° C., about 50-150° C., about 50-130° C., about 50-110° C., about 50-90° C., about 50-70° C., about 70-150° C., about 70-130° C., about 70-110° C., about 70-90° C., about 90-150° C., about 90-130° C., about 90-110° C., about 110-150° C., about 110-130° C., or about 130-150° C.

Process of Preparing Compounds of Formula (1) and (4)

Disclosed herein is a process for preparing a compound of Formula (1),

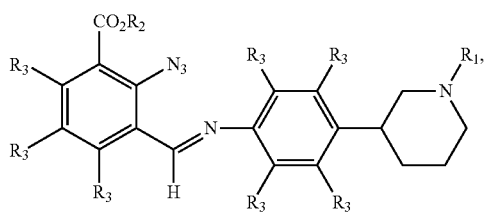

(1)

or a salt thereof, comprising: contacting a compound of Formula (2),

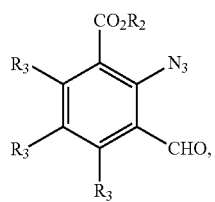

(2)

or a salt thereof, with a compound of Formula (3),

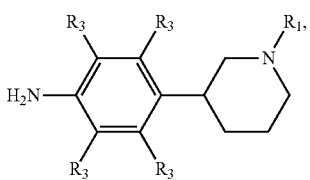

(3)

or a salt thereof,
wherein:
R$_1$ is H or an amine protecting group;
R$_2$ is H, C$_{1-10}$ alkyl, C$_{1-10}$ haloalkyl, or aryl; and
each R$_3$ is independently H, halogen, C$_{1-10}$ alkyl, C$_{1-10}$ haloalkyl, or aryl.

In some embodiments, the compound of Formula (1) or salt thereof has a structure of Formula (4):

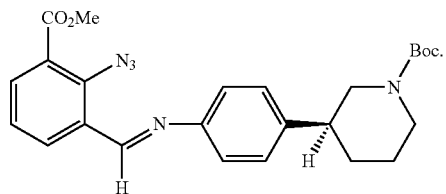

(4)

Process of Preparing Compounds of Formula (5) and (6)

Disclosed herein is a process for preparing a compound of Formula (5),

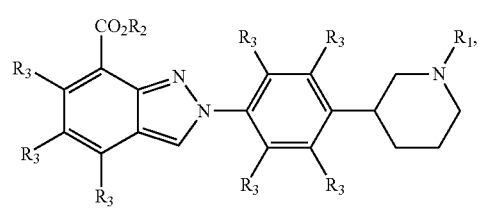

(5)

or a salt thereof, comprising: contacting a compound of Formula (1),

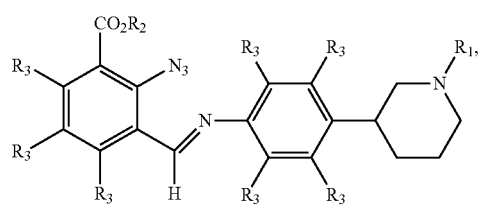

(1)

or a salt thereof, with a catalyst,
wherein:
R$_1$ is H or an amine protecting group;
R$_2$ is H, C$_{1-10}$ alkyl, C$_{1-10}$ haloalkyl, or aryl; and
each R$_3$ is independently H, halogen, C$_{1-10}$ alkyl, C$_{1-10}$ haloalkyl, or aryl.

In some embodiments, the compound of Formula (5) or salt thereof has a structure of Formula (6):

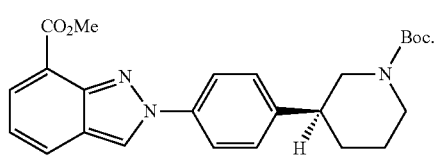

(6)

Process of Preparing Compounds of Formula (7) and (8)

Disclosed herein is a process for preparing a salt of Formula (7),

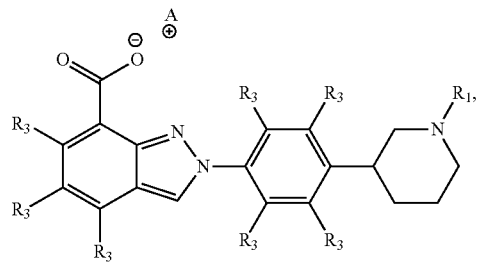

(7)

comprising: contacting a compound of Formula (5),

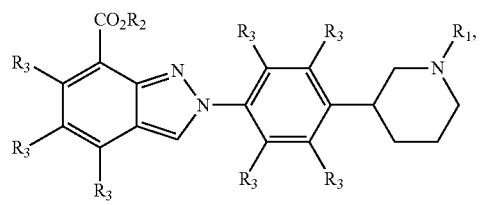

(5)

or a salt thereof, with a metal hydroxide,
wherein:
$R_1$ is H or an amine protecting group;
$R_2$ is H, $C_{1-10}$ alkyl, $C_{1-10}$ haloalkyl, or aryl;
each $R_3$ is independently H, halogen, $C_{1-10}$ alkyl, $C_{1-10}$ haloalkyl, or aryl; and
A is a cation.

In some embodiments, the cation is an inorganic cation or organic cation. In some embodiments, the cation is a metal cation. In some embodiments, the metal cation is an alkali metal cation. In some embodiments, the alkali metal cation is lithium cation.

In some embodiments, the salt of Formula (7) has a structure of Formula (8):

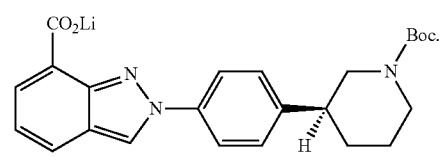

(8)

Process of Preparing Compounds of Formula (9) and (10)

Disclosed herein is a process for preparing a compound of Formula (9),

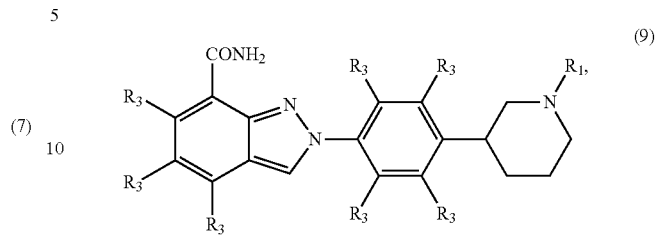

(9)

or a salt thereof, comprising: contacting a compound of Formula (7),

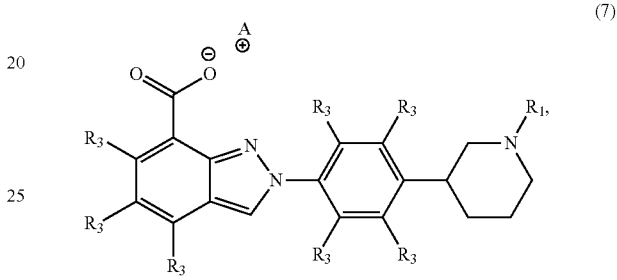

(7)

or a salt thereof, with a coupling reagent and ammonium hydroxide,
wherein:
$R_1$ is H or an amine protecting group;
$R_2$ is H, $C_{1-10}$ alkyl, $C_{1-10}$ haloalkyl, or aryl; each $R_3$ is independently H, halogen, $C_{1-10}$ alkyl, $C_{1-10}$ haloalkyl, or aryl; and
A is a cation.

In some embodiments, the cation is a metal cation. In some embodiments, the metal cation is an alkali metal cation. In some embodiments, the alkali metal cation is lithium cation. In some embodiments, the coupling reagent is CDI.

In some embodiments, the compound of Formula (9) or salt thereof has a structure of Formula (10):

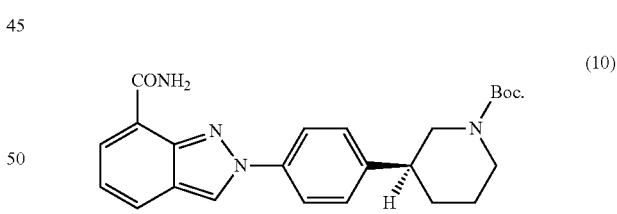

(10)

Process of Preparing Compounds of Formula (11) and (12)

Disclosed herein is a process for preparing a salt of Formula (11),

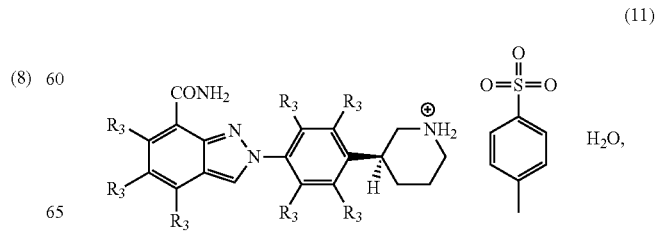

(11)

comprising: contacting a compound of Formula (9),

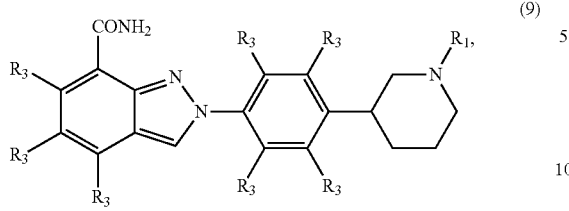

or a salt thereof, with para-toluene sulfonic acid monohydrate (pTSA.H$_2$O),
wherein:
R$_1$ is H or an amine protecting group;
R$_2$ is H, C$_{1-10}$ alkyl, C$_{1-10}$ haloalkyl, or aryl; and
each R$_3$ is independently H, halogen, C$_{1-10}$ alkyl, C$_{1-10}$ haloalkyl, or aryl.

In some embodiments, the salt of Formula (11) has a structure of Formula (12):

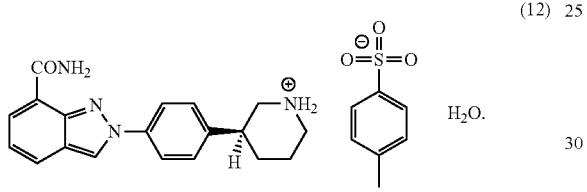

Process of Preparing Enantiomerically Enriched (S)-Niraparib Tosylate Monohydrate Disclosed herein is a process for preparing an enantiomerically enriched (S)-niraparib tosylate monohydrate of Formula (12),

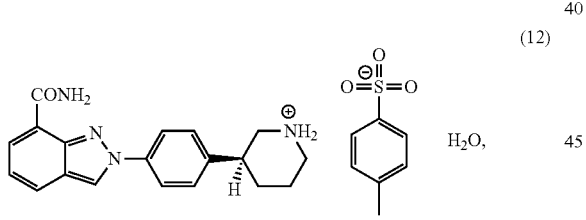

comprising:
a) contacting a mixture comprising (R)-niraparib tosylate monohydrate and (S)-niraparib tosylate monohydrate with water and a first organic solvent;
b) separating (S)-niraparib tosylate monohydrate from the mixture by filtration to form an enantiomerically enriched (S)-niraparib tosylate monohydrate; and
c) contacting the enantiomerically enriched (S)-niraparib tosylate monohydrate with a second organic solvent, water, or any combination thereof to form a crystalline form of the enantiomerically enriched (S)-niraparib tosylate monohydrate.

In some embodiments, the process further comprises wet milling the crystalline form of the enantiomerically enriched (S)-niraparib tosylate monohydrate. In some embodiments, the process further comprising annealing the enantiomerically enriched (S)-niraparib tosylate monohydrate using one or more temperature cycles.

Also disclosed herein is a process for preparing an enantiomerically enriched (S)-niraparib tosylate monohydrate of Formula (12),

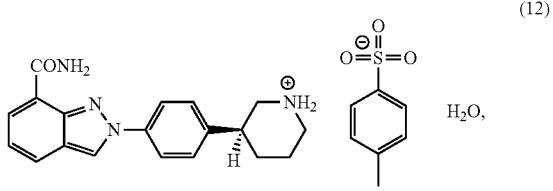

comprising:
a) contacting a salt of Formula (13),

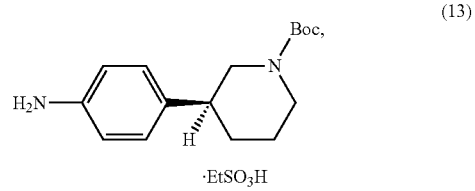 [SMILES: "·EtSO3H" ; CC(C)(C)OC(=O)N1CCC[C@@H](c2ccc(N)cc2)C1]

with sodium hydroxide and toluene, to form a compound of Formula (14),

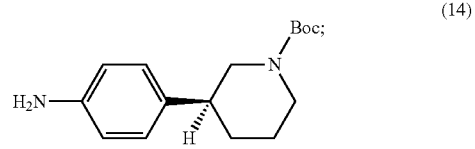 [SMILES: CC(C)(C)OC(=O)N1CCC[C@@H](c2ccc(N)cc2)C1]

b) contacting a compound of Formula (15),

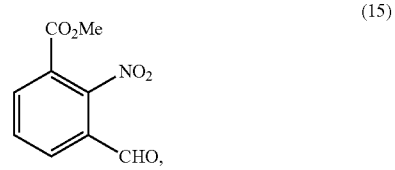 [SMILES: COC(=O)c1cccc(C=O)c1[N+](=O)[O-]]

with sodium azide, ethyl acetate and DMSO, to form a compound of Formula (16),

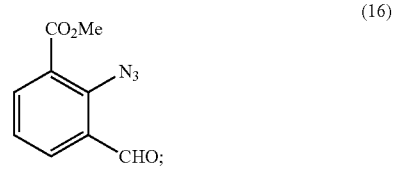

c) contacting the compound of Formula (14) with the compound of Formula (16) and TFA, to form a compound of Formula (4),

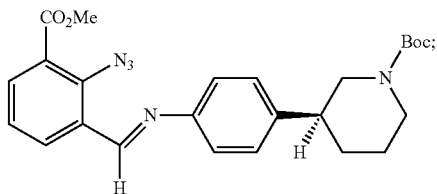

d) contacting the compound of Formula (4) with copper (II) trifluoromethanesulfonate (Cu(OTf)$_2$), THF and toluene, to form a compound of Formula (6),

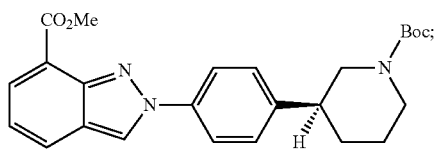

e) contacting the compound of Formula (6) with lithium hydroxide and ethanol, to form a salt of Formula (8),

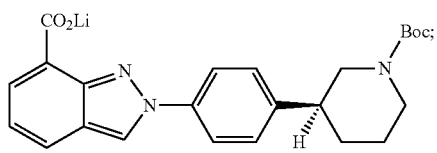

f) contacting the salt of Formula (8) with CDI, TFA, N,N-dimethylformide (DMF), and ammonium hydroxide, to form a compound of Formula (10),

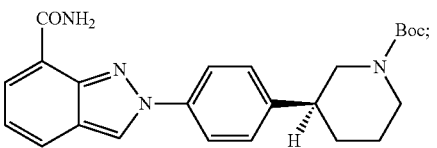

g) contacting the compound of Formula (10) with p-Toluenesulfonic acid monohydrate (pTSA.H$_2$O) and THF, to form (S)-niraparib tosylate monohydrate of Formula (12),

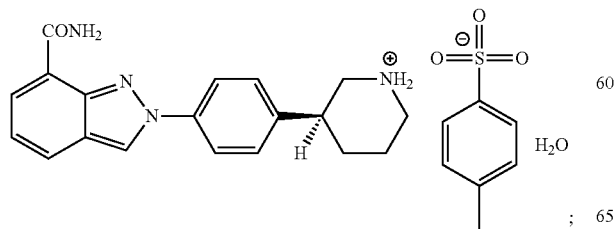

h) contacting the (S)-niraparib tosylate monohydrate of Formula (12) with acetonitrile and water, to form a mixture;

i) separating (S)-niraparib tosylate monohydrate from the mixture by filtration, to form an enantiomerically enriched (S)-niraparib tosylate monohydrate; and j) contacting the enantiomerically enriched (S)-niraparib tosylate monohydrate with DMSO and water, to form a crystalline form of the enantiomerically enriched (S)-niraparib tosylate monohydrate.

In some embodiments, the process further comprises wet milling the crystalline form of the enantiomerically enriched (S)-niraparib tosylate monohydrate. In some embodiments, the process further comprises annealing the enantiomerically enriched (S)-niraparib tosylate monohydrate using one or more temperature cycles.

Salts of Formula (7) and (8)

Disclosed herein is a salt of Formula (7),

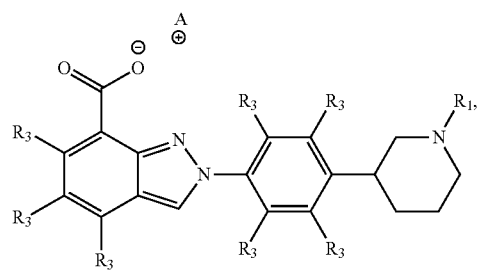

wherein:

$R_1$ is H or an amine protecting group;

each $R_3$ is independently H, halogen, $C_{1-10}$ alkyl, $C_{1-10}$ haloalkyl, or aryl; and A is a cation.

In some embodiments, the cation is a metal cation. In some embodiments, the metal cation is an alkali metal cation. In some embodiments, the alkali metal cation is lithium cation.

In some embodiments, the salt of Formula (7) has a structure of Formula (8):

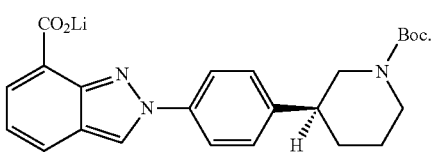

Process of Preparing a Compound of Formula (17)

Disclosed herein is a process for preparing a compound of Formula (17),

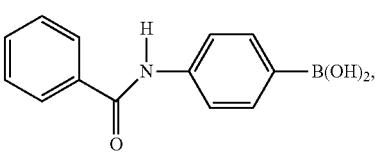

or a salt thereof, comprising: contacting a compound of Formula (18),

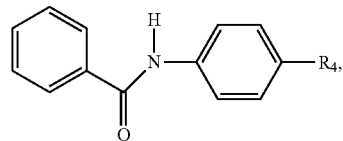
(18)

or a salt thereof, with n-butyl lithium and triisopropyl borate (B(Oi-Pr)$_3$), wherein R$_4$ is a leaving group. In some embodiments, the process further comprises a hydrolysis reaction.

In some embodiments, the process comprises contacting a compound of Formula (19),

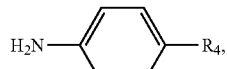
(19)

or a salt thereof, with benzoyl chloride and an organic compound, to form the compound of Formula (18) or salt thereof, wherein R$_4$ is a leaving group.

Process of Preparing Compounds of Formula (20) and (26)

Disclosed herein is a process for preparing a compound of Formula (20),

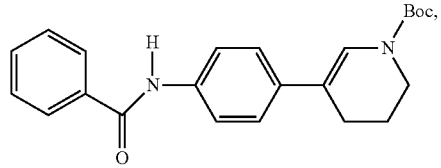
(20)

or a salt thereof, comprising: contacting a compound of Formula (17),

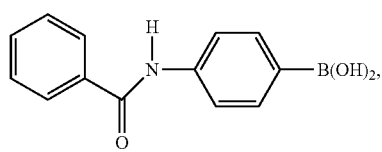
(17)

or a salt thereof, with a salt of Formula (21),

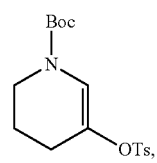
(21)

in presence of a catalyst.

In some embodiments, the contacting the compound of Formula (17), or the salt thereof further comprises contacting a salt of Formula (22),

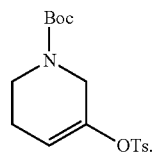
(22)

Disclosed herein is also a process for preparing a compound of Formula (26),

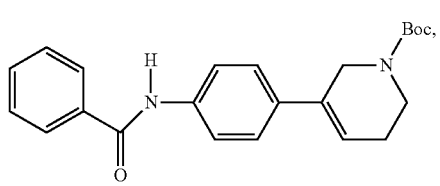
(26)

or a salt thereof, comprising: contacting a compound of Formula (17),

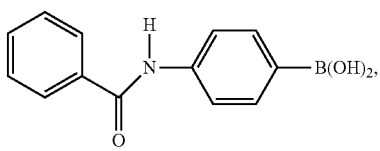
(17)

or a salt thereof, with a salt of Formula (22),

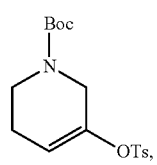
(22)

in presence of a catalyst.

Process of Preparing Compounds of Formula (23) and (24)

Disclosed herein is a process for preparing a compound of Formula (23),

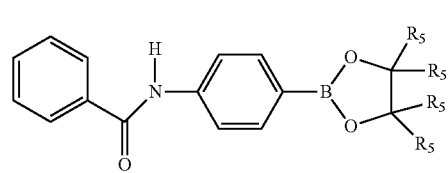
(23)

or a salt thereof, comprising: contacting a compound of Formula (17),

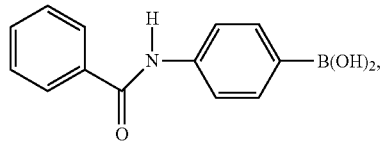
(17)

or a salt thereof, with

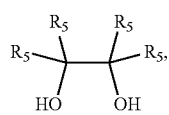

wherein each $R_5$ is independently H or $C_{1-3}$ alkyl.

In some embodiments, the compound of Formula (23) or salt thereof has a structure of Formula (24),

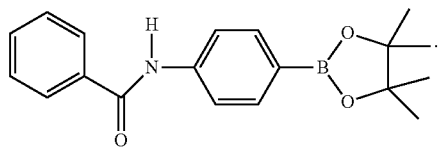
(24)

Process of Preparing Compounds of Formula (20) and (26)

Disclosed herein is a process for preparing a compound of Formula (20),

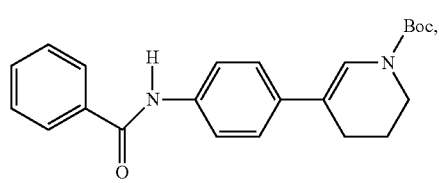
(20)

or a salt thereof, comprising: contacting the compound of Formula (23),

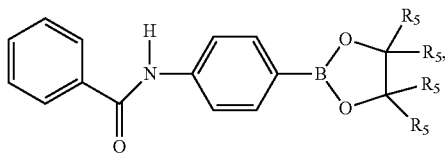
(23)

or the salt thereof, with a salt of Formula (21),

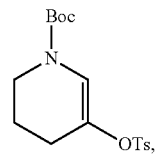
(21)

in the presence of a catalyst.

In some embodiments, the contacting the compound of Formula (23), or salt thereof further comprises contacting a salt of Formula (22),

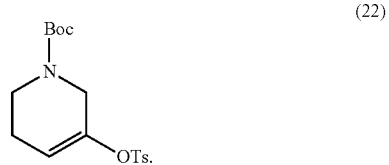 [SMILES: Cc1ccc(S(=O)(=O)OC2=CCCN(C(=O)OC(C)(C)C)C2)cc1]
(22)

Disclosed herein is also a process for preparing a compound of Formula (26),

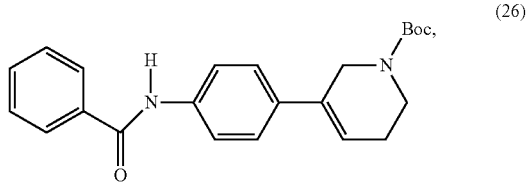 [SMILES: CC(C)(C)OC(=O)N1CCC=C(c2ccc(NC(=O)c3ccccc3)cc2)C1]
(26)

or a salt thereof, comprising: contacting the compound of Formula (23),

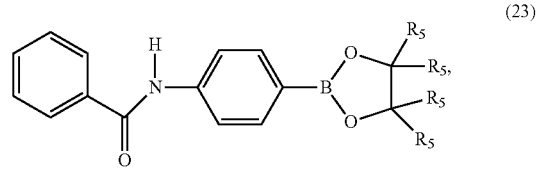
(23)

or the salt thereof, with a salt of Formula (22),

(22)

in the presence of a catalyst.

Process of Preparing a Compound of Formula (25)

Disclosed herein is a process for preparing a compound of Formula (25),

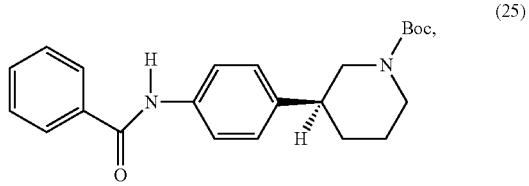 [SMILES: CC(C)(C)OC(=O)N1CCC[C@@H](c2ccc(NC(=O)c3ccccc3)cc2)C1]
(25)

or a salt thereof, comprising: contacting a compound of Formula (20),

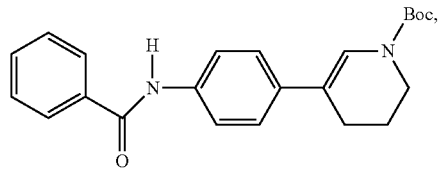

or a salt thereof, with a ligand.

In some embodiments, the process further comprises contacting a compound of Formula (26),

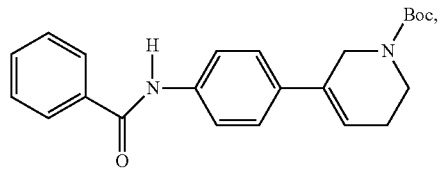

or a salt thereof, with the ligand.

Process of Preparing a Compound of Formula (14)

Disclosed herein is a process for preparing a compound of Formula (14),

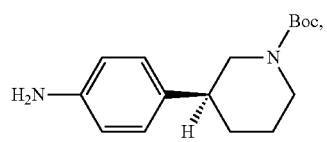

or a salt thereof, comprising:
contacting a compound of Formula (25),

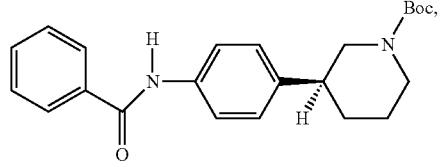

or a salt thereof, with a base.

Process of Preparing a Salt of Formula (13)

Disclosed herein is a process for preparing a salt of Formula (13),

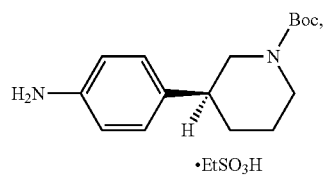

comprising: contacting a compound of Formula (14),

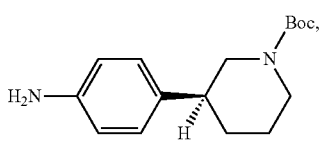

or a salt thereof, with an acid.

Process of Preparing Compounds of Formula (21) and (22)

Disclosed herein is a process for preparing a compound of Formula (21),

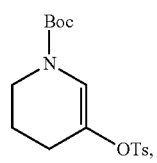

or a salt thereof, comprising: oxidizing a compound of Formula (28),

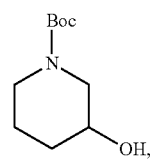

or a salt thereof, with an oxidizing agent, to form a compound of Formula (29),

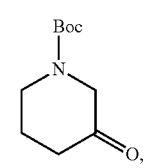

or a salt thereof; and
contacting the compound of Formula (29) or salt thereof, with p-Toluenesulfonic anhydride. In some embodiments, the oxidizing agent is 2,2,6,6-tetramethylpiperidine-1-oxyl (TEMPO).

In some embodiments, the contacting the compound of Formula (29) or salt thereof results in formation of a mixture of the compound of Formula (21), and the compound of Formula (22),

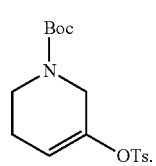

Process of Preparing Compounds of Formula (30) and (25)

Disclosed herein is a composition of Formula (30),

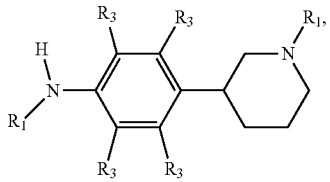
(30)

or a salt thereof,
wherein:
each $R_1$ is independently H or an amine protecting group; and
each $R_3$ is independently H, halogen, $C_{1-10}$ alkyl, $C_{1-10}$ haloalkyl, or aryl.

In some embodiments, the compound or salt thereof has a structure of Formula (25):

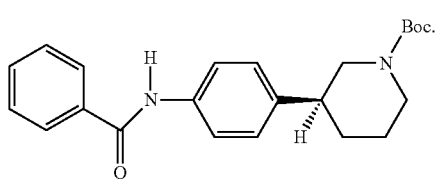
(25)

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

Example 1—Synthesis of methyl 3-formyl-2-nitrobenzoate (Aldehyde A)

Example 1 describes synthesis of the compound methyl 3-formyl-2-nitrobenzoate (Aldehyde A) (also see FIG. 1):

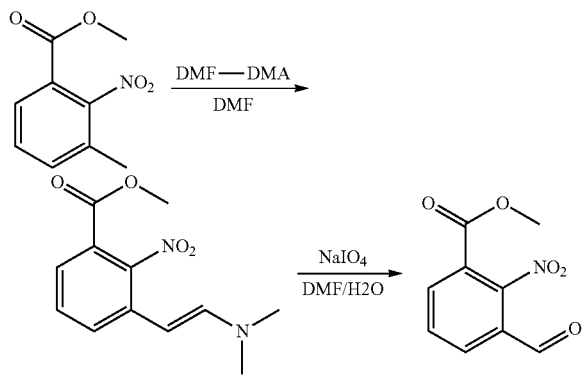

A two-step reaction was performed for the synthesis of the compound methyl 3-formyl-2-nitrobenzoate.

Reaction 1.1: Synthesis of methyl-3-(2-(dimethylamino)vinyl)-2-nitrobenzoate

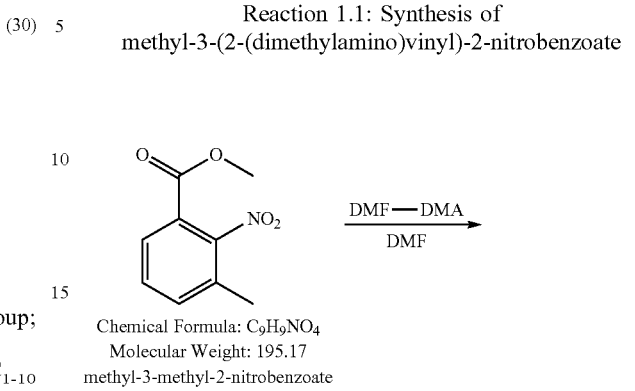

Chemical Formula: $C_9H_9NO_4$
Molecular Weight: 195.17
methyl-3-methyl-2-nitrobenzoate

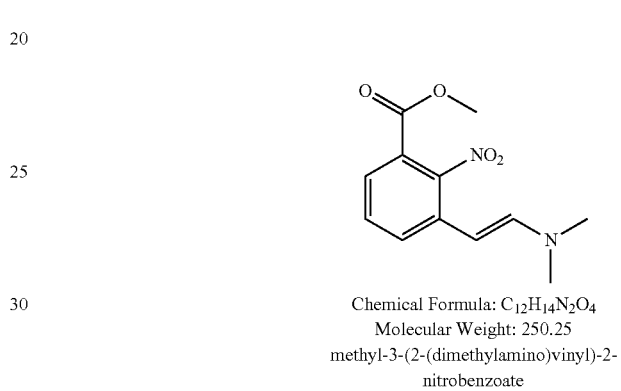

Chemical Formula: $C_{12}H_{14}N_2O_4$
Molecular Weight: 250.25
methyl-3-(2-(dimethylamino)vinyl)-2-nitrobenzoate A clean reactor was charged with dimethyl formamide (DMF, 530 grams) and methyl-3-methyl-2-nitrobenzoate (100.0 g, 1.0 eq). The mixture was agitated and heated to 130° C. under nitrogen protection. N,N Dimethylformamide dimethyl acetal (DMF-DMA, 130 g, eq) was added dropwise while maintaining the temperature at 130°. The mixture was stirred at 130° C. for 16 hours, and was sampled for reaction completion. When complete, the mixture was cooled to 5° C. and stirred for 2 hours. The product was isolated by filtration and was washed with water (5×130 mL). The wet cake (83.3 g, 65%) was used directly for the next step. $^1$H NMR (400 MHz, CDCl3) 7.58 (m, 2H), 7.31 (m, 1H), 6.88 (d, J=13.4 Hz, 1H), 4.94 (d, J=13.4 Hz, 1H) 3.891 (s, 3H), 2.875 (s, 6H).

Reaction 1.2: Synthesis of methyl 3-formyl-2-nitrobenzoate

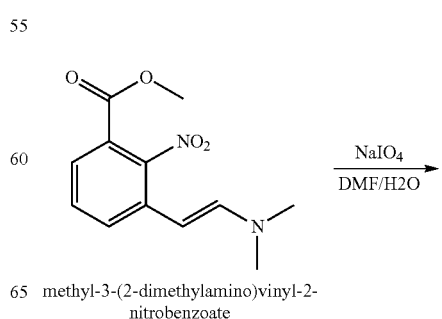

methyl-3-(2-dimethylamino)vinyl-2-nitrobenzoate

-continued

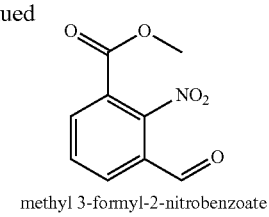

methyl 3-formyl-2-nitrobenzoate

A clean, dry reactor was charged with DMF (525 g) and the crude intermediated (83.3 g, 330 mmol, 1.0 eq) obtained in the previous step. The mixture was stirred at 33° C. until all of the solids had dissolved. The clear solution was removed and bottled. Deionized water (640 g) was charged to the reactor and the temperature was adjusted to 30° C. Solid sodium periodate (NaIO4, 149.9 g, 2.1 eq) was added and the temperature was adjusted to 45° C. The solution of the enamine intermediate in DMF was charged to an overhead dropping funnel and was added slowly to the stirred aqueous sodium periodate. Once the addition was complete, the reaction mixture was stirred at 45° C. for 4 hours. Ethyl acetate (933 g) was added and the mixture was stirred for 1 hour at 35° C. The triphasic mixture was filtered. The filtrate was transferred to a clean reactor. The filtered solids were slurried with ethyl acetate, the mixture was filtered and the ethyl acetate filtrate was combined with the initial filtrate. The combined filtrates were stirred for 30 minutes at 35° C.

The agitation was stopped and the mixture allowed to settle for 30 minutes. The layers were separated and the aqueous phase was mixed with ethyl acetate (225 g), cooled to 5° C. and stirred for 30 minutes. The solids which formed were removed by filtration. The layers were separated and the process was repeated. The resulting organic solution was washed twice with aqueous sodium chloride solution (350 kg 1.5% NaCl). The final organic solution was tested negative to starch iodide paper. The organic solution mixed with activated carbon (20 g), and was stirred for 6 hours at 75° C. The mixture was cooled to 45° C. and filtered through diatomaceous earth. The ethyl acetate filtrate was concentrated under reduced pressure (<40° C.) to a final volume between 125 and 167 mL). The mixture was cooled to 0° C. and stirred for 6 hours. The product was isolated by filtration and was dried under vacuum at 25° C. affording Aldehyde A as a clean light yellow colored solid (56.6 g, 80%). $^1$H NMR (400 MHz, CDCl3) 9.95 (s, 1H), 8.27 (d, J=8.0 Hz, 1H), 8.16 (d, J=8.0 Hz, 1H), 7.77 (t, J=8.0 Hz, 1H), 3.93 (s, 3H).

Example 2—Synthesis of (S)-4-(1-(tert-butoxycarbonyl)piperidin-3-yl)benzenaminium Ethanesulfonate (Aniline ESA Salt)

Figure 2:
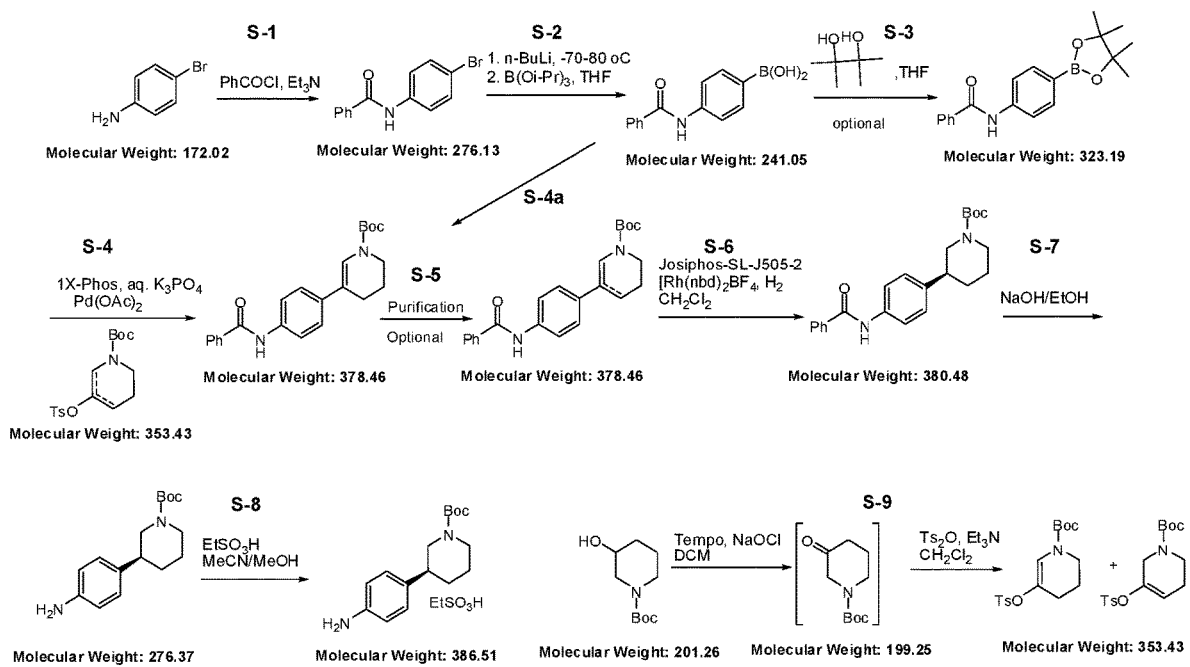
FIG. 2 shows the synthesis of the compound (S)-4-(1-(tert-butoxycarbonyl)piperidin-3-yl)benzenaminium ethanesulfonate (Aniline ESA salt).

Example 2 describes synthesis of the compound (S)-4-(1-(tert-butoxycarbonyl)piperidin-3-yl)benzenaminium ethanesulfonate (Aniline ESA salt) (also see FIG. 2):

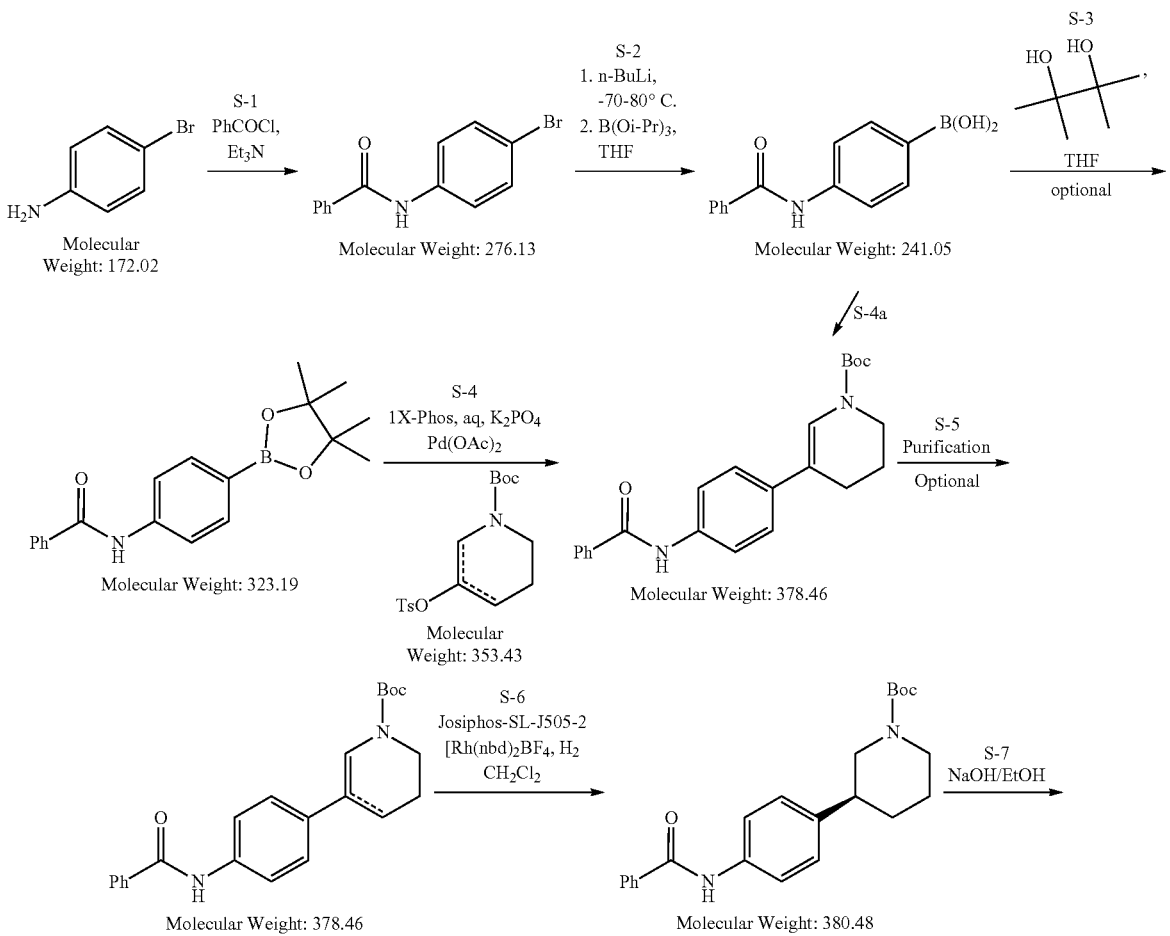

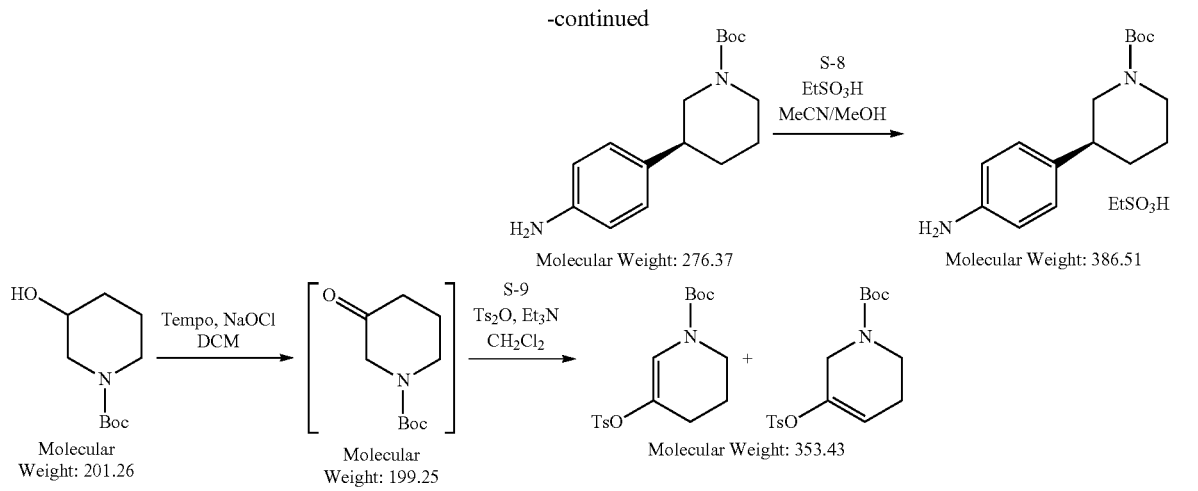

A multi-step reaction was performed for the synthesis of the compound (S)-4-(1-(tert-butoxycarbonyl)piperidin-3-yl)benzenaminium ethanesulfonate (Aniline ESA salt).

Reaction S-1: Synthesis of N-(4-bromophenyl)benzamide

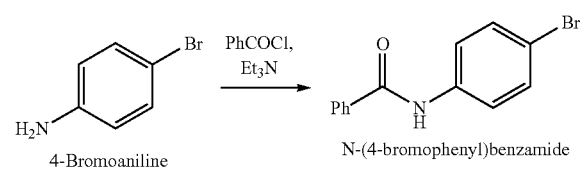 [SMILES: Nc1ccc(Br)cc1 ; O=C(Nc1ccc(Br)cc1)c1ccccc1]

4-Bromoaniline (100 g, 581 mmol, 1.0 eq) was charged to a clean reactor. Tetrahydrofuran (THF, 410 mL) was added and the mixture was stirred until clear solution was formed. Triethylamine (TEA, 60 g, 593 mmol, 1.02 eq) was added and the mixture was cooled to about −5° C. Benzoyl chloride (80 g, 569 mmol, 0.98 eq) was added dropwise while maintaining the temperature at about 0° C. The mixture was then stirred for 2 hours at room temperature. Water (1000 g) was slowly added dropwise at room temperature. After stirring for 4 hours at room temperature, the crude solid product was isolated by filtration, and the filter cake was washed with water (2×200 mL). The wet cake was isolated and dried under vacuum at NMT 50° C. for 40 hours to afford 156 g (97%) of N-(4-bromophenyl)benzamide. $^1$H NMR (400 MHz, DMSO-d6) 10.383 (s, 1H), 7.97 (d, J=8.5, 2H), 7.79 (d, J=8.5, 2H), 7.61-7.52 (m, 5H)); 13C NMR (DMSO-d6, 100.61 MHz); 166.136, 139.063, 135.191, 132.173, 131.896, 128.884, 128.155, 122.687, 115.797; HRMS m/z: [M+H]+ Calcd for C13H11BrNO 276.0019. Found 276.0025.

Reaction S-2: Synthesis of (4-Benzamidophenyl)boronic Acid

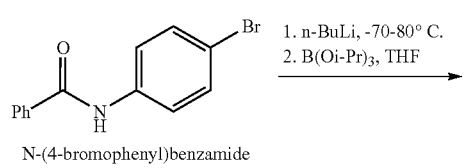

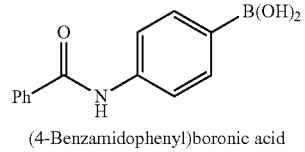

(4-Benzamidophenyl)boronic acid

A reactor was charged with N-(4-bromophenyl)benzamide (100 g, 362 mmol, 1.0 eq) and THF (2090 mL). The mixture was stirred at about 25° C. until solids were dissolved and then cooled to about −85-−70° C. A separate reactor was charged with 2.5 n-butyl lithium in hexane (104 g, 375 mmol, 1.0 eq) which was slowly added to the solution of the bromo aniline in THF while keeping the internal temperature between −85 and −70° C. The resulting mixture was stirred at −85° C. and −70° C. for an additional 30 minutes. A second portion of 2.5n-n-butyl lithium in hexane (149 g, 538 mmol, 1.5 eq) while maintaining the internal temperature between −85 and −70° C. After the addition was complete, the mixture was stirred at about −85-−70° C. for about 30 minutes and triisopropyl borate (270 g, 1.4 mol, 4.0 eq) was slowly added while maintaining the temperature at −85-−70° C. Next, the mixture was stirred at −85-−70° C. until the reaction reached completion. Acetic Acid (200 g, 3.3 moles, 9.1 eq) was added while maintaining the temperature between −10 and 10° C. The mixture was stirred at 0° C. for 4 hours (pH ca 5), and was concentrated to (550 mL, 5.5 V) under reduced pressure (at about 45° C.). The temperature of the mixture was adjusted to 20° C. and water (1050 mL) was added. The mixture was stirred for 4 hours at 20° C. and the resulting crude solid product was isolated by filtration. The crude product (ca 146 g) was charged to a reactor along with water (650 g) and methyl t-Butyl ether (MTBE, 450 g). The slurry was stirred at 20° C. for about 4 hours. The mixture was filtered and the resulting solid was washed successively with water and MTBE. The filter cake was dried under vacuum for 48 h at about 55° C. to afford 80 g (92%) of the desired boronic acid. $^1$H NMR (400 MHz, DMSO-d$_6$) 10.251 (s 1H), 7.94 (d, J=7.2, 4H), 7.74 (d, J=3.2, 4H), 7.58-7.54 (m, 1H); $^{13}$C NMR (DMSO-d$_6$, 100.61 MHz); 166.085, 141.309, 135.461, 135.184, 132.042, 128.855, 128.141, 119.508; HRMS m/z: [M+H]$^+$ Calcd for C$_{13}$H$_{13}$BNO$_3$ 241.1019. Found 241.1015.

Reaction S-3 (Optional Step): Synthesis of N-(4-(4,4,5,5-tetramethyl-1,3,2-dioxaborolan-2-yl)phenyl)benzamide

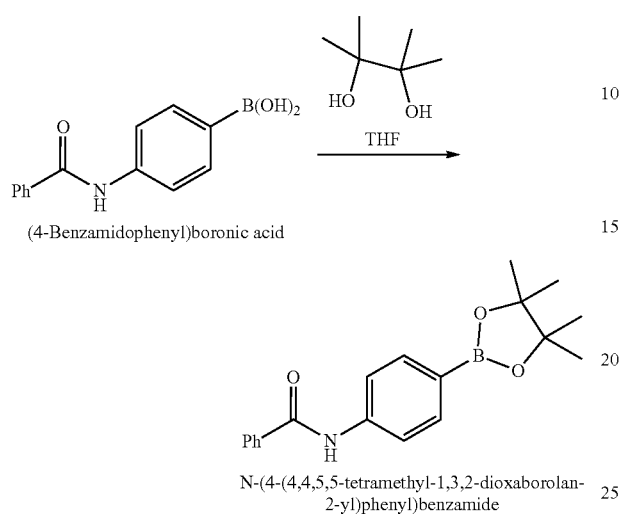

(4-Benzamidophenyl)boronic acid

N-(4-(4,4,5,5-tetramethyl-1,3,2-dioxaborolan-2-yl)phenyl)benzamide

A reactor was charged with THF (720 g) followed by the boronic acid intermediate ((4-Benzamidophenyl)boronic acid) (100 g, 1.0 eq), and pinacol (60 g, 1.2 eq). The mixture was stirred and heated to 65° C. for 4 hours. The mixture was heated to 75° C. and was concentrated to 4.0 volumes (V) under atmospheric pressure. The mixture was cooled to 50° C. and was concentrated to 2.0 V under reduced pressure at about 50° C. n-Heptane (1030 mL) was slowly added maintaining the temperature at 50° C. The mixture was stirred for 3 hours at 50° C., was cooled to 5° C. over 2 hours, and stirred at 5° C. for 6 hours. The product was isolated by filtration and was washed with n-heptane. The wet cake was dried under vacuum at 45° C. affording the desired product as an off-white solid (139 g, 100%). $^1$H NMR (400 MHz, CDCl$_3$) 7.89 (d, J=7 Hz, 3H), 7.85 (d, J=8 Hz, 2H), 7.70 (d, J=8 Hz, 2H), 7.57 (d, J=7 Hz, 2H), 7.28 (dd, J=7 Hz, J=8 Hz, 2H), 1.374 (s, 12H); $^{13}$C NMR (DMSO-d$_6$, 100.61 MHz); 166.201, 142.541, 135.607, 135.301, 132.144, 128.863, 128.192, 119.741, 83.948, 25.173; HRMS m/z: [M+H]$^+$ Calcd for C$_{19}$H$_{22}$BNO$_3$ 323.1802. Found 323.1798.

Reaction S-9: Synthesis of tert-butyl 5-(tosyloxy)-3,4-dihydropyridine-1(2H)-carboxylate and tert-butyl 5-(tosyloxy)-3,6-dihydropyridine-1(2H)-carboxylate

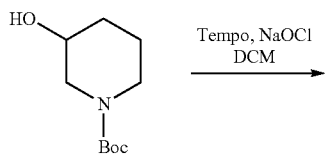

Molecular Weight: 201.26
1-Boc-3-hydroxypiperidine

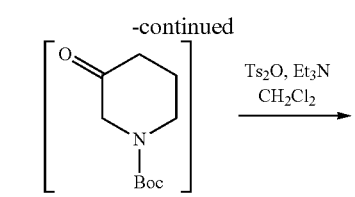

Molecular Weight: 199.25
tert-butyl 3-oxopiperidine-1-carboxylate

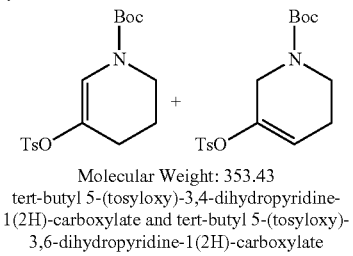

Molecular Weight: 353.43
tert-butyl 5-(tosyloxy)-3,4-dihydropyridine-1(2H)-carboxylate and tert-butyl 5-(tosyloxy)-3,6-dihydropyridine-1(2H)-carboxylate A clean reactor was charged with DCM (800 g) and the 1-Boc-3-hydroxypiperidine(100 g, 1.0 eq). The mixture was stirred and cooled to 0° C. Aqueous sodium bicarbonate solution was added (500 g) and the mixture was stirred at 0° C. Solid potassium bromide (2 g, 0.03 eq) was added while maintaining a temperature at about 5° C. 2,2,6,6-tetramethylpiperidine-1-oxyl (TEMPO, 100 mg, 0.001 eq) was added and the mixture allowed to stand for 30 minutes at 0° C. Aqueous sodium hypochlorite (10%, 450 g, 1.2 eq) was slowly added over 5 hours at 0° C. After the addition was complete, the mixture was stirred at 0° C. for 30 minutes. Aqueous sodium sulfite (20% 490 g, 1.6 eq) was added over 1 hour at 0° C., and the mixture was stirred for 40 minutes at 0° C. and settled and the layers were separated. The aqueous phase was extracted twice with DCM (500 g) at 0° C., and the combined organic phases were washed with water (500 g) at 0° C. The layers were separated and the organic phase was concentrated to 450 mL by vacuum distillation at about 25° C. followed by addition of DCM (670 mL). This solution was cooled and was used directly for the next step.

The mixture prepared above was cooled and DCM (670 g) was added. p-Toluene sulfonic anhydride (180 g, 1.1 eq) was added slowly at 0° C. followed by trimethylamine (TEA 95 g, 1.9 eq), also at 0° C. The mixture was stirred at 0° C. for 1 hour. After warming to 25° C., the mixture was stirred for 14 hours. The mixture was then cooled to 5° C. and water (530 g) was added over 1 hour at 5° C., and the mixture was stirred for 1 hour at 5° C. The layers were separated and the organic phase was washed twice with water (300 g). The organic phase was treated with activated charcoal (10 g) in DCM (40 g). After stirring for 4 hours at room temperature, the mixture was filtered through a layer of silica gel (5 g). The filtrate was washed twice with water (310 g) and was concentrated to 250 mL by vacuum distillation at about 50° C. Isopropyl alcohol (430 g) was added and the mixture was concentrated to 250 mL under vacuum at about 50° C. The temperature was adjusted to 50° C. and the mixture was stirred until a clear solution had formed. Water (290 g) was slowly added over 3 hours at 50° C., mixture was stirred at 50° C. for 90 minutes and then cooled to 15° C. over 6 hours and held there for an additional 6 hours. The crude product was isolated by filtration and the filter cake was washed with IPA/Water (1:2 w/w, 10 g). The wet cake was returned to the reactor and was slurried with 220 mL of a mixture of IPA/Water (1:2 w/w) for 30 minutes at 15° C. The product was isolated by vacuum filtration, was washed with IPA/Water (1:2 w/w, 10 g), and was dried under vacuum at 45° C. to provide the desired product (134.8 g, 77%). $^1$H NMR (400 MHz, CDCl$_3$) 7.82 (d, 2H), 7.35 (d, 2H), 6.75 (s, 0.3H) 6.48 (s, 0.7H), 3.42 (t, J=5.6, 2H), 2.46 (s, 3H), 2.30 (m, 2H), 1.81 (t, J=5.6, 2H), 1.40 (s, 9H); $^{13}$C NMR (CDCl3, 100.61 MHz); 151.560, 145.086, 133.004, 132.362, 129.847, 129.723, 128.534, 128.359, 121.199, 120.654, 81.243, 41.761, 40.580, 28.352, 28.134, 25.290, 21.710, 21.134, 20.828; HRMS m/z: [M+NH$_4$]$^+$ Calcd for C$_{17}$H$_{27}$N$_2$O$_5$S, 371.1635. Found 371.1632.

Reaction S-4: Synthesis of tert-Butyl 5-(4-benzamidophenyl)-3,6-dihydropyridine-1(2H)-carboxylate and tert-Butyl 5-(4-benzamidophenyl)-3,4-dihydropyridine-1(2H)-carboxylate

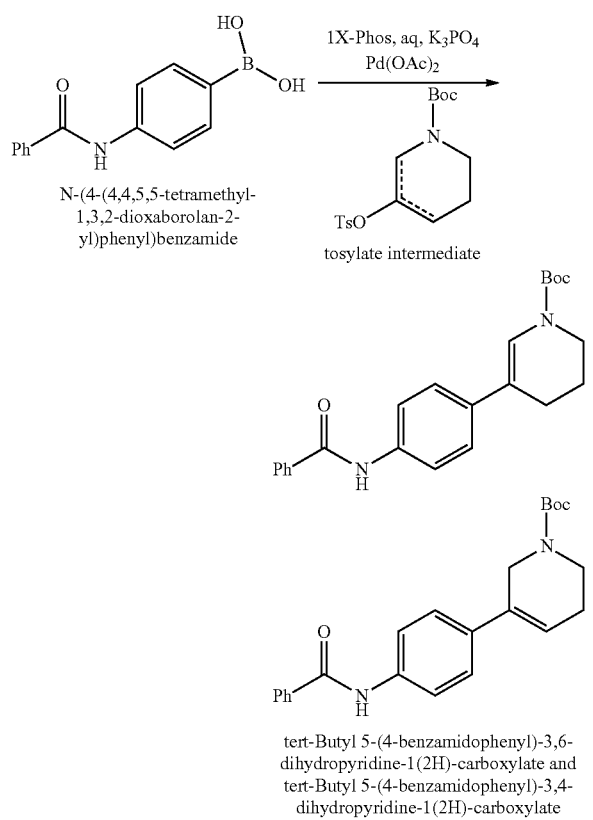

tert-Butyl 5-(4-benzamidophenyl)-3,6-dihydropyridine-1(2H)-carboxylate and tert-Butyl 5-(4-benzamidophenyl)-3,4-dihydropyridine-1(2H)-carboxylate A reactor was charged with the tosylate intermediate (tert-butyl 5-(tosyloxy)-3,4-dihydropyridine-1(2H)-carboxylate and tert-butyl 5-(tosyloxy)-3,6-dihydropyridine-1(2H)-carboxylate, 112 g, 317 mmol, 1.00 eq) and THF (884 mL). The temperature of the mixture was adjusted to 20° C. and the boronic acid derivative (80.0 g, 332 mmol, 1.05 eq) was added, followed by an aqueous solution of potassium phosphate (30%, 571 g). XPhos (680 mg, 0.005 eq) was added and the reaction mixture was deoxygenated by five vacuum/nitrogen purge cycles. Palladium acetate (224 mg, 0.004 eq) was added followed by further vacuum/nitrogen purge cycles. The mixture was stirred and held at 65° C. for 10 hours. After adjusting the temperature to 25° C., the phases were split, and the organic phase was concentrated to about 250 mL under vacuum followed by addition of DCM (1050 mL). The resulting mixture was stirred at room temperature for about 2 hours and then filtered through the filter aid, diatomaceous earth. The filtrate was washed twice with water. The organic phase was treated with activated charcoal (18 g). The mixture was stirred at 25° C. for 2 hours and filtered through diatomaceous earth to provide a clear solution. The solution was concentrated to about 300 mL under reduced pressure (internal temperature <50° C.). 2-Me THF (440 mL) was added and the mixture was concentrated under reduced pressure ((internal temperature <50° C.). n-Heptane (1450 mL) was added and the mixture was stirred for about 2 hours at 45° C., and then at about 15° C. The product was isolated by filtration and the filter cake was washed with a mixture of 2-MeTHF/n-Heptane (1:3 v/v) followed by n-Heptane. The wet product was dried under vacuum at 40 to 60° C. to afford 92 g (86.2%). $^1$H NMR (400 MHz, CDCl$_3$) 8.20 (br s, 1H), 7.87 (d, 2H), 7.64-7.33 (mm, 8H), 6.19 (br s, 0.13H), 4.23 (br s, 0.27H), 3.58 (m, 2H), 2.44 (br s, 2H), 1.97 (br s, 2H), 1.55 (s, 9H); $^{13}$C NMR (CDCl$_3$, 100.61 MHz); 165.822, 165.742, 155.024, 152.960, 152.443, 136.081, 135.0.46, 131.735, 128.717, 127.076, 125.560, 124.867, 124.0634, 122.847, 122.505, 120.383, 120.281, 115.818, 81.054, 80.893, 42.293, 41.265, 28.527, 28.367, 24.174, 23.788, 21.710; HRMS m/z: [M+H]$^+$ Calcd for C$_{23}$H$_{27}$N$_2$O$_3$ 379.2016. Found 379.2016.

In addition, a few different bases, solvents and ligands (e.g., phosphine ligands) were tested and the result was shown below:

| prod % | Base | Solvent | Ligand |
|---|---|---|---|
| 88.4 | Cs$_2$CO$_3$ | N,N-dimethylformide (DMF) | X-Phos |
| 87.2 | K$_3$PO$_4$ | DMF | X-Phos |
| 86.9 | Cs$_2$CO$_3$ | t-butanol | X-Phos |
| 86.2 | Cs$_2$CO$_3$ | DMF | xantphos |
| 85.9 | K$_3$PO$_4$ | DMF | Davephos |
| 85.9 | K$_3$PO$_4$ | t-butanol | Davephos |
| 84.9 | K$_3$PO$_4$ | Dimethoxyethane (DME) | Davephos |
| 83.5 | K$_3$PO$_4$ | t-butanol | X-Phos |
| 82.1 | K$_3$PO$_4$ | DME | X-Phos |
| 81.2 | K$_3$PO$_4$ | DME | JohnPhos |
| 81.2 | Cs$_2$CO$_3$ | DME | Davephos |
| 80.2 | Cs$_2$CO$_3$ | acetonitrile | xantphos |

Notes:
1) product % = 100*product/(all major peaks in LC traces), LC area percent
2) 5 mg tosylate, boronic acid to tosylate 1.3:1, 4 mol % Pd(OAc)$_2$, Ligand/Pd = 1.25 for xantphos, 2.0 for X-Phos, 2.0 equiv of base rel. to boronic acid, 200 uL solvent, 90° C. 18 h.
3) Solvent contains 25% water Reaction S-4a: Synthesis of tert-Butyl 5-(4-benzamidophenyl)-3,6-dihydropyridine-1(2H)-carboxylate and tert-Butyl 5-(4-benzamidophenyl)-3,4-dihydropyridine-1(2H)-carboxylate

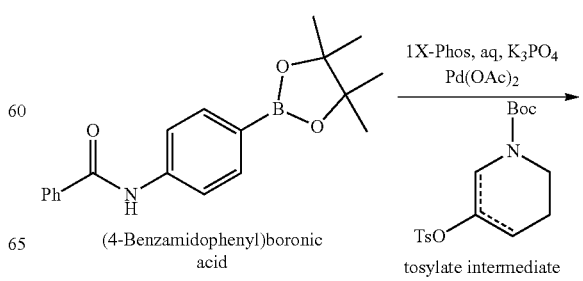

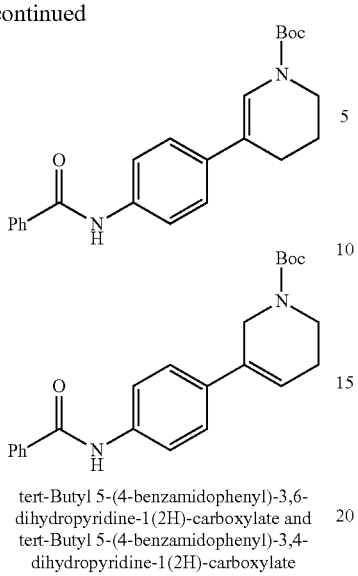

tert-Butyl 5-(4-benzamidophenyl)-3,6-
dihydropyridine-1(2H)-carboxylate and
tert-Butyl 5-(4-benzamidophenyl)-3,4-
dihydropyridine-1(2H)-carboxylate A reactor was charged with THF (639 mL) and the tosylate intermediate (tert-butyl 5-(tosyloxy)-3,4-dihydropyridine-1(2H)-carboxylate and tert-butyl 5-(tosyloxy)-3,6-dihydropyridine-1(2H)-carboxylate) (100 g, 284 mmol, 1.00 eq) and the pinacol borane intermediate (96 g, 297 mmol, 1.05 eq). The mixture was stirred and the temperature was adjusted to 20° C. A solution of potassium phosphate (192 g) in water (360 mL) was freshly prepared and added dropwise. XPhos (640 mg, 0.005 eq) was added and the reaction mixture was deoxygenated by vacuum/nitrogen purge cycles. Palladium acetate (250 mg, 0.004 eq) was added followed by performing further vacuum/nitrogen purge cycles. The mixture was heated to 65° C. and held at this temperature for 10 hours. The temperature was adjusted to 25° C. and the phases were split. The organic phase was concentrated to about 300 mL under vacuum followed by addition of DCM (1011 mL). The resulting mixture was stirred at room temperature for about 2 hours and then filtered through the filter aid (diatomaceous earth). The filtrate was washed twice with water. The organic phase was treated with activated charcoal (15 g) at 25° C. for 2 hours and filter aid diatomaceous earth was charged. The mixture was filtered and the filter cake was washed with DCM. The solution was concentrated under reduced pressure at about 50° C. 2-Me-THF (550 mL) was added and the mixture concentrated to 350 mL under reduced pressure at about 50° C. n-Heptane (850 mL) was added at 45° C. The mixture was stirred for 2 hours at 45° C. and cooled to 15° C. over 4-6 hours. The product was isolated by filtration and the filter cake was washed with a mixture of 2-MeTHF/n-Heptane (1:3 v/v, 200 g) followed by n-Heptane (300 g). The wet product was dried under vacuum at 40 to 60° C. to afford 98.8 g (91%) of product. See data above for characterization.

Reaction S-5 (optional): Purification of tert-Butyl
5-(4-benzamidophenyl)-3,6-dihydropyridine-1(2H)-
carboxylate and tert-Butyl 5-(4-benzamidophenyl)-
3,4-dihydropyridine-1(2H)-carboxylate The crude unsaturated aniline derivative (tert-Butyl 5-(4-benzamidophenyl)-3,6-dihydropyridine-1(2H)-carboxylate and tert-Butyl 5-(4-benzamidophenyl)-3,4-dihydropyridine-1(2H)-carboxylate, 100 g) was charged to a reactor followed by acetonitrile (ACN, 316 g). The mixture was stirred for one hour at 75° C. followed by addition of acetonitrile (143 mL). Water (291 g) was slowly added at 75° C. The mixture was stirred for 2 hours at 75° C. and then slowly cooled to 4° C. over 6 hours, and held at 4° C. for an additional 5 hours. The product was isolated by filtration and the filter cake was washed with acetonitrile:water (2:1, 75 g) followed by water (100 g). The wet cake was dried under vacuum for 48 hours at 45° C. to afford the purified product (96.0 g, 96%).

Reaction S-6 and S-7: Synthesis of tert-butyl (S)-3-
(4-benzamidophenyl)piperidine-1-carboxylate

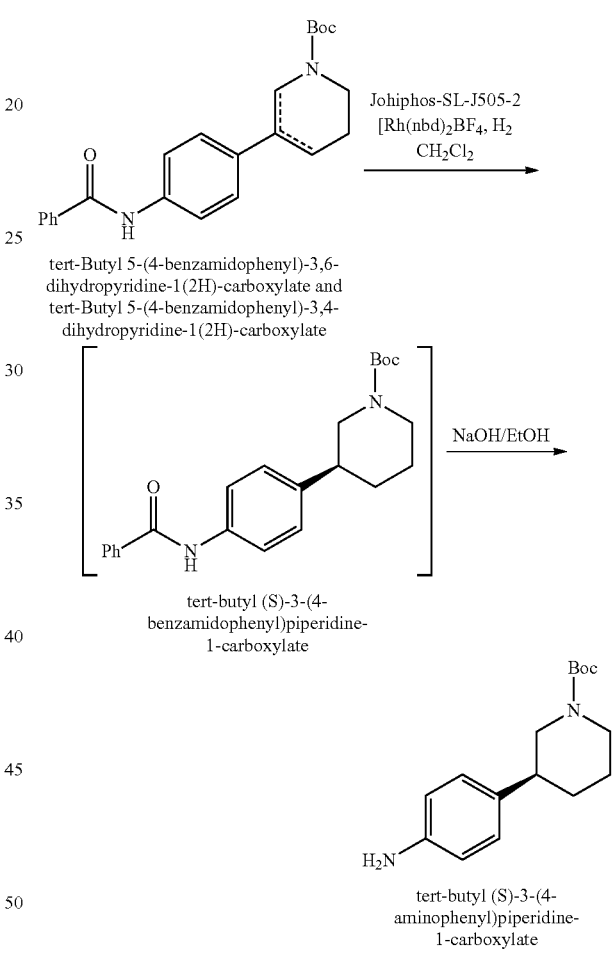

A hydrogenation reactor was charged with the unsaturated aniline (tert-Butyl 5-(4-benzamidophenyl)-3,6-dihydropyridine-1(2H)-carboxylate and tert-Butyl 5-(4-benzamidophenyl)-3,4-dihydropyridine-1(2H)-carboxylate, 100 g), Josiphos-SL-J505-2 (770 mg), $Rh(nbd)_2BF_4$ catalyst (500 mg) and DCM (320 g). The mixture was degassed by successive vacuum/nitrogen backfill cycles. The mixture was saturated with hydrogen gas by successive vacuums/hydrogen pressurizations to 1.55 MPa (224 psi) cycles. The temperature of the mixture was heated to 40° C. and the mixture stirred for 19 hours under 1.55 MPa (224 psi) of hydrogen pressure. The mixture was cooled to 20° C., was degassed by five successive vacuums/nitrogen backfill cycles. If the reaction was incomplete, another hydrogenation cycle was performed. Upon completion of the reaction, DCM (231 g) was added and the mixture was filtered to remove the catalyst. The filter cake was rinsed with DCM (58 g) and the filtrate was concentrated under vacuum to 210 mL at about 55° C. Ethanol (350 mL) was added and the mixture was concentrated under vacuum to 420 mL at about 55° C. and repeated a further two times. Ethanol (115 mL) was added along with aqueous sodium hydroxide (30%, 347 g). The mixture was heated at 80° C. until completion of the reaction. The mixture was cooled to 15° C. and water (996 g) was added. The mixture was stirred at 15° C. for 1.5 hours and the product was isolated by filtration. The filter cake was washed with water and the wet cake was dried under vacuum at 50° C. to afford the product (71 g, 96%). $^1$H NMR (400 MHz, CDCl$_3$), 7.02 (d, J=8 Hz, 2H), 6.62 (d, J=8 Hz, 2H), 4.135 (br s, 2H), 3.601 (s, 2H), 2.69-2.557 (m, 3H), 1.74, (m, 1H), 1.611 (m, 1H), 1.57 (m, 2H), 1.529 (s, 9H); $^{13}$C NMR (CDCl$_3$, 100.61 MHz); 154.892, 144.947, 133.667, 127.893, 115.206, 51.017, 44.243, 43.861, 41.703, 31.947, 28.710, 28.520, 25.611; FIRMS m/z: [M+H]$^+$ Calcd for C$_{12}$H$_{17}$N$_2$O$_2$ 221.1285. Found 221.1282.

In addition, a few more chiral ligands and solvents were tested and the result was shown below:

| Item | Ligand | Solvent | Conversion (%) | EE (%) |
|---|---|---|---|---|
| 1 | Josiphos-SL-J505-2 | CH$_2$Cl$_2$ | >99 | 79 |
| 2 | Josiphos-SL-J013 | Me—THF | 12 | 73 |
| 3 | Josiphos-SL-J212 | Me—THF | 36 | 82 |
| 4 | Josiphos-SL-J011 | Me—THF | <5 | Not detected |
| 5 | Josiphos-SL-N012 | MeOH | 90 | 60 |

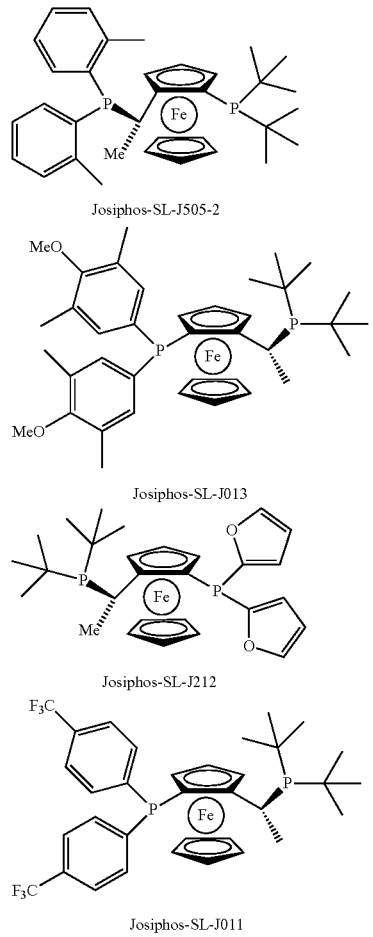

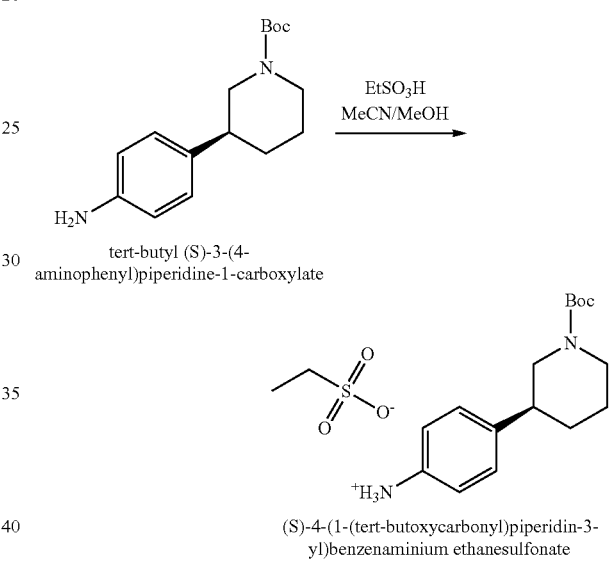

Reaction S-8: Synthesis of (S)-4-(1-(tert-butoxycarbonyl)piperidin-3-yl)benzenaminium Ethanesulfonate A reactor was charged with tert-butyl (S)-3-(4-aminophenyl)piperidine-1-carboxylate (100 g, 362 mmol, 1.0 eq) and acetonitrile (959 g). The temperature was adjusted to 25° C. and microcrystalline cellulose (10 g) was added. The mixture was stirred for 1.5 hours and was filtered. The filter cake was rinsed with acetonitrile (489 g). The filtrate was cooled to 0° C. and methanol (126 g) was added. A solution of ethane sulfonic acid (42.6 g, 1.07 eq) in acetonitrile (87 g) was prepared. A portion of this solution (20%) was added to the reaction mixture at 0° C. Seeds of the aniline ethanesulfonate (260 mg) were added. The resulting mixture was stirred at about 20° C. for 2 hours followed by the slow addition of the remainder of the ethanesulfonate solution (106.08 g) over 13 hours at 0° C. The mixture was stirred for 8 hours at 0° C. and the crystalline product was isolated by filtration. The filter cake was washed with a mixture of methanol and acetonitrile (4%) and subsequently acetonitrile. The wet cake was dried under vacuum for 20 hours at 20° C. to provide the product as an off white solid (108.5 g, 77.6%). $^1$H NMR (400 MHz, CDCl$_3$); 9.90 (br s, 3H), 7.49 (d, J=8 Hz, 2H), 7.25 (d, J=8 Hz, 2H), 4.12 (br s, 2H), 1.98 (m, 1H), 1.74 (m, 1H), 1.61-1.56 (m, 2H), 1.45 (s, 9H), 1.106 (t, J=7 Hz, 3H): $^{13}$C NMR (DMSO-d$_6$, 100.61 MHz); 154.324, 143.759, 131.021, 128.826, 123.452, 79.172, 45.654, 41.936, 31.670, 28.556, 25.450, 25.363, 10.299; HRMS m/z: [M+H]+ Calcd for $C_{12}H_{17}N_2O_2$ 221.1285. Found 221.1282.

In addition, the preparation of ESA salt from 4 different solvent systems was able to upgrade from ee to ranging from 85-98% ee. The result was shown below:

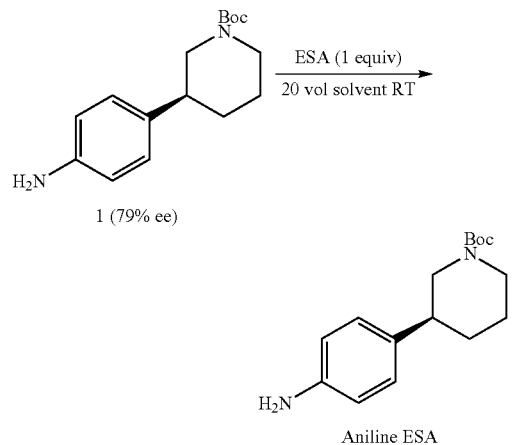

2: Solvent = MeCN (85% ee, 89% yield)
3: Solvent = 7.5% MeOH/MeCN (95% ee, 70% yield)
4: Solvent = 10% MeOH/MeCN (95% ee, 56% yield)
5: Solvent = 40% DCM/MeCN (98% ee, 51% yield)

TABLE 1

ESA salt formation with ee upgrade at room temperature

| Solvent | Time (h) | Volume (mL/g) | SM ee (%) | Isolated solid ee (%) | Isolated recovery yield (%) |
|---|---|---|---|---|---|
| MeCN | 0.5[b] | 14.3[a] | 79 | 85 | 89 |
| 7.5% MeOH/MeCN | 1[b] | 15.4[a] | 79 | 94.5 | 68 |
| 7.5% MeOH/MeCN | 19[b] | 15.4[a] | 79 | 95.5 | 72 |
| 10% MeOH/MeCN | 1[b] | 15[a] | 79 | 95 | 56 |
| 40% DCM/MeCN | 1[b] | 15[a] | 79 | 98 | 51 |

Figure 3:
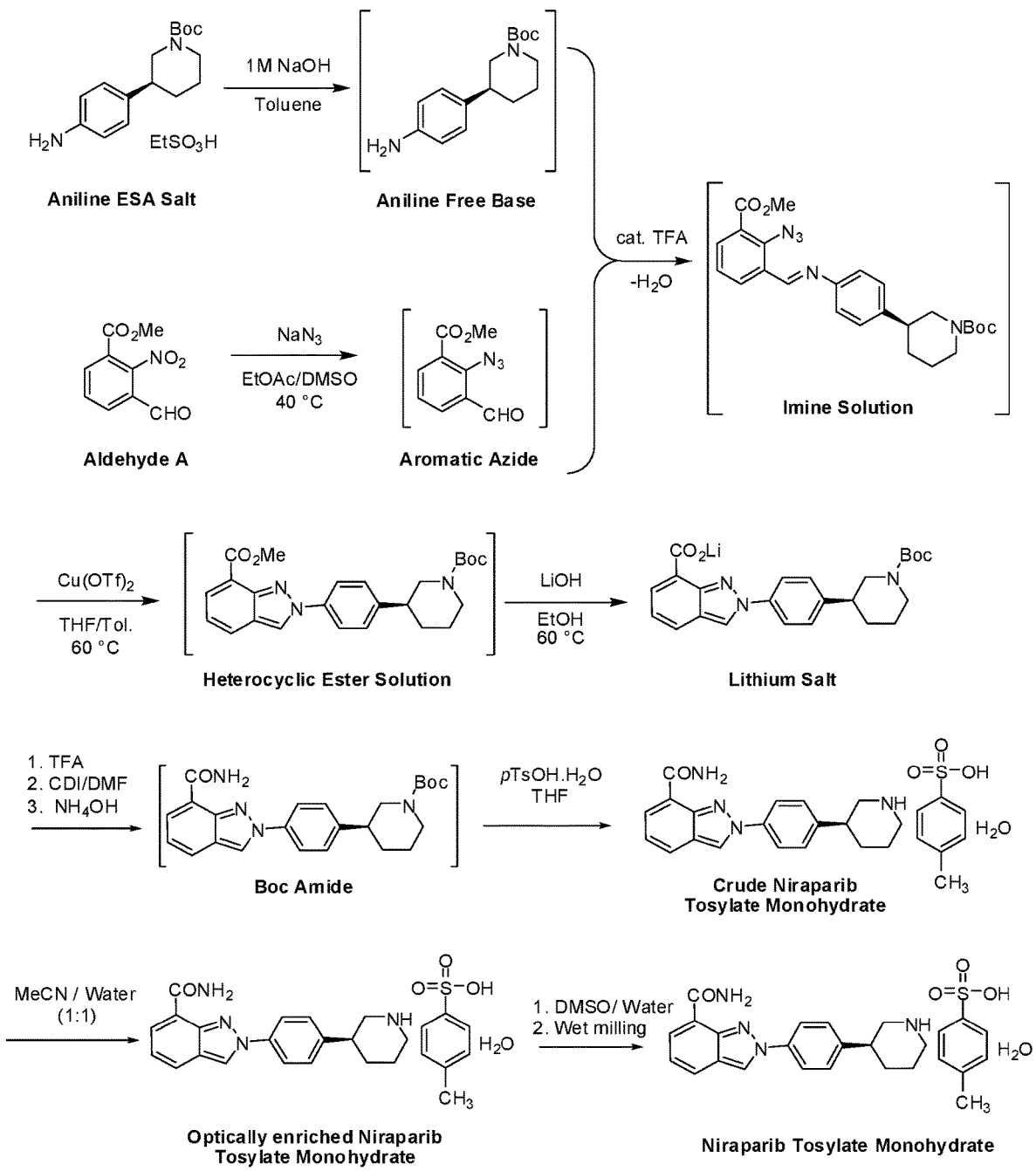
FIG. 3 shows the synthesis of the compound niraparib tosylate monohydrate.

[a]Volume relative to salt (20 volume relative to free base)
[b]Indicate slurry time after salt formation is complete Example 3—Synthesis of Niraparib Tosylate Monohydrate Example 3 describes synthesis of the compound niraparib tosylate monohydrate (also see FIG. 3):

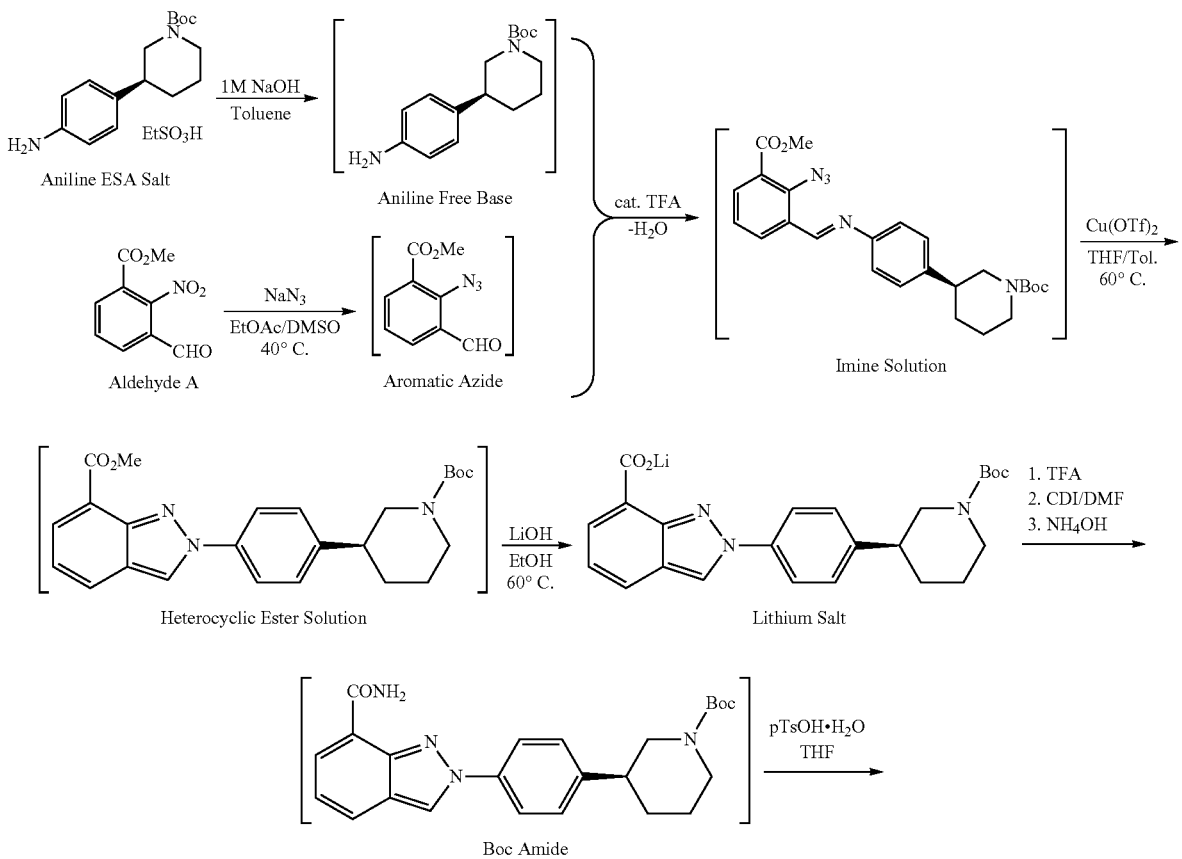

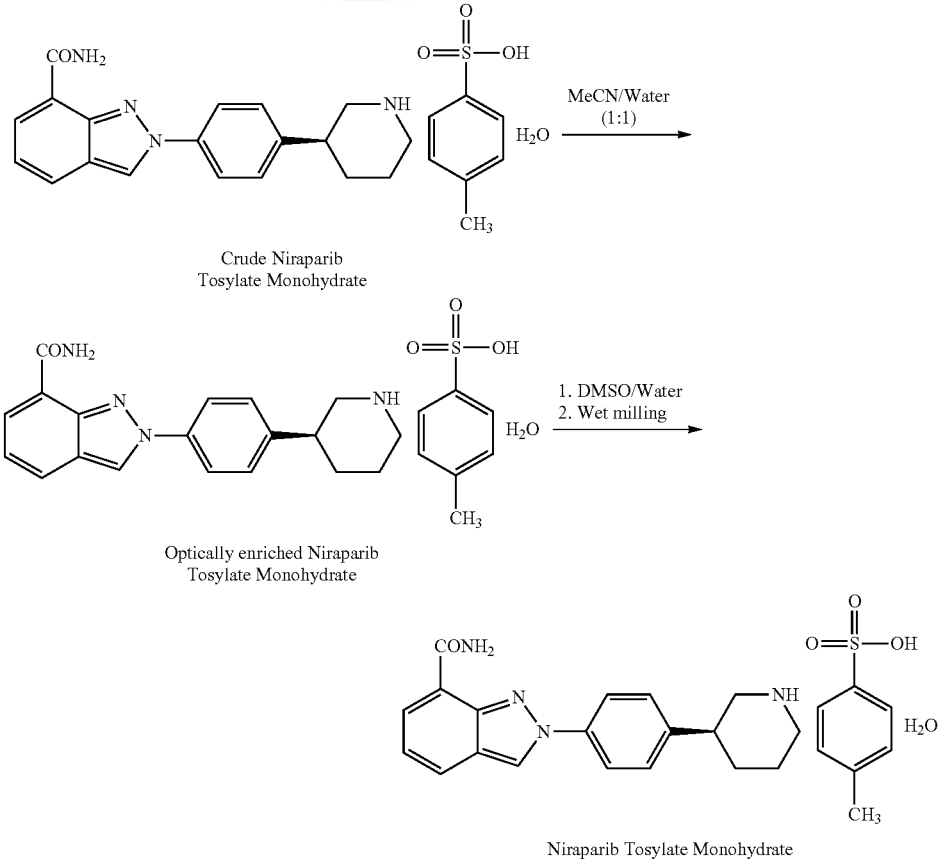

Crude Niraparib Tosylate Monohydrate

Optically enriched Niraparib Tosylate Monohydrate

Niraparib Tosylate Monohydrate

Synthesis of tert-butyl (S)-3-(4-aminophenyl)piperidine-1-carboxylate (Aniline Free Base)

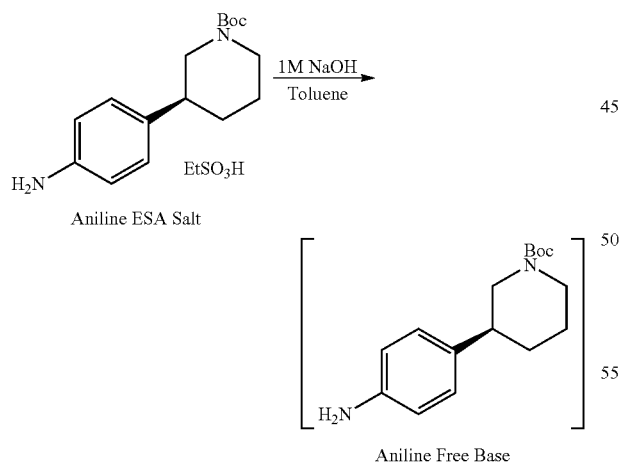

Aniline ESA Salt

Aniline Free Base

Aqueous sodium hydroxide (1N, 649 mL, 675 g, 1.2 eq, 3.13×) was slowly added to a chilled (15° C.) suspension of the aniline ESA salt (210 g, 541 mmol) in toluene (2730 g). The mixture was stirred for 1 hour and the layers were allowed to settle. The phases were separated and the organic phase was warmed to 23° C. and washed with water (730 mL, typically 3 times) until the pH of the aqueous phase was between 7 and 8. A light yellow solution was obtained (ca. 2830 g) providing a near quantitative yield of the aniline freebase.

Synthesis of methyl 2-azido-3-formylbenzoate (Aromatic Azide)

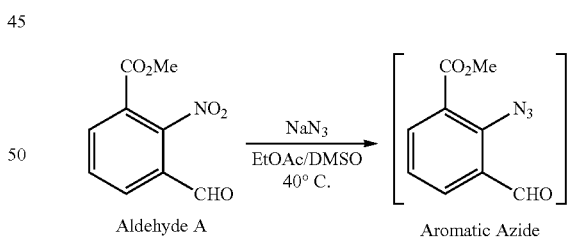

Aldehyde A

Aromatic Azide

The mixture of sodium azide (32.6 g, 1.05 eq) in DMSO (440 g) was stirred at about 25° C. for 20 minutes followed by addition of ethyl acetate (450 g) and methyl 3-formyl-2-nitrobenzoate (Aldehyde A, 100 g, 1.0 eq). The mixture was heated to 40° C. and stirred for about 3 hours under nitrogen purge. Ethyl acetate (450 g) and water (500 g) were then added to the stirred mixture at 35° C. The phases were separated and the lower (aqueous phase) was extracted with ethyl acetate (450 g) at 35° C. The combined organic phases were washed with water at 20° C. to afford the product as a solution in ethyl acetate.

Synthesis of tert-Butyl (S,E)-3-(4-((2-azido-3-(methoxycarbonyl)benzylidene)amino)phenyl)piperidine-1-carboxylate (Imine)

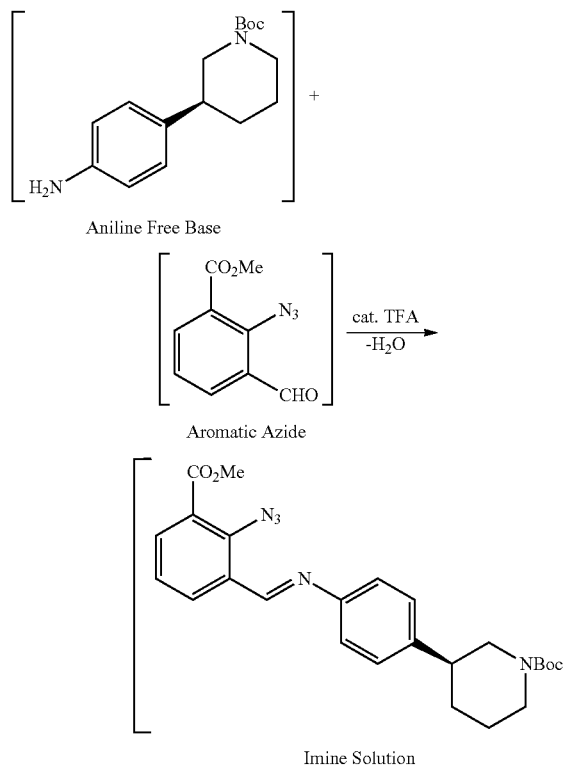

Aniline Free Base

Aromatic Azide

Imine Solution

To the aromatic azide solution in ethyl acetate prepared above was added 98% of the aniline freebase toluene solution (97% of the solution by weight) prepared in the previous step. The mixture was concentrated to about 2 L. under vacuum at 45° C. The mixture was cooled to room temperature, and trifluoroacetic acid (55 mg, 0.001 eq) was added. The mixture was stirred at room temperature for about one hour before concentrating to about 1 L under vacuum at about 50° C. After cooling to room temperature, the solution was used directly in the next step.

Synthesis of methyl (S)-2-(4-(1-(tert-butoxycarbonyl)piperidin-3-yl)phenyl)-2H-indazole-7-carboxylate (Heterocyclic Ester)

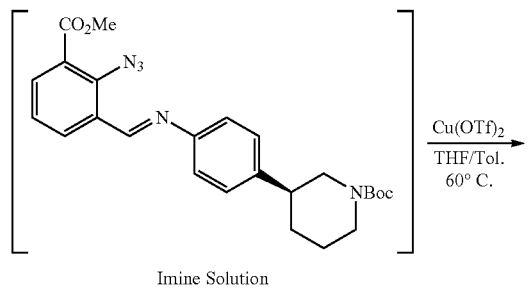

Imine Solution

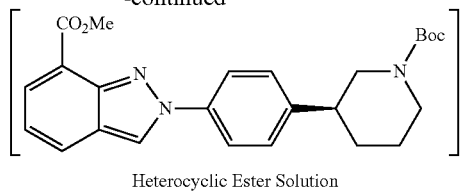

Heterocyclic Ester Solution

To a stirred suspension of copper (II) Triflate (900 mg, 0.005 eq) in THF (1.78 L) at 60° C. was added drop wise the solution of the imine prepared above over 4 hours. After the addition was complete, the mixture was stirred for about 3 hours at 60° C. and was then cooled to room temperature. The solvent was exchanged to ethanol by the addition of ethanol (1 L) and concentration to about 0.8 L under vacuum at 50° C. This was repeated three times to provide an ethanolic solution of the heterocyclic ester solution. This solution was used directly for the next step.

Synthesis of Lithium (S)-2-(4-(1-(tert-butoxycarbonyl)piperidin-3-yl)phenyl)-2H-indazole-7-carboxylate (Lithium Salt)

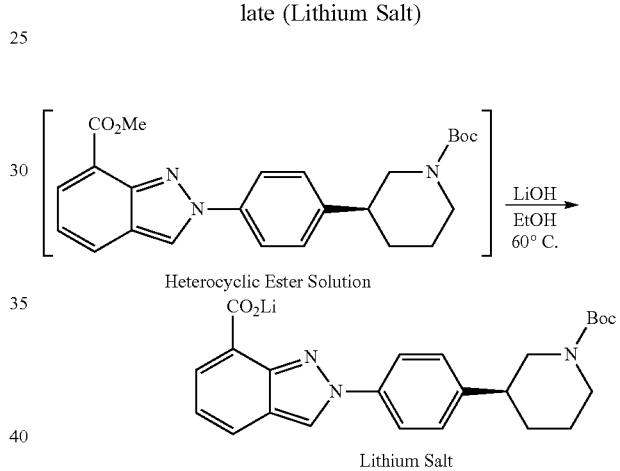

Heterocyclic Ester Solution

Lithium Salt

A stirred suspension of lithium hydroxide monohydrate (22.4 g, 1.2 eq) in ethanol (560 mL) was heated to 60° C. The solution of the heterocyclic ester in ethanol (ca 0.8 L, prepared above) was added drop wise over 4 hours while maintaining the temperature at 60° C. The mixture was stirred at 60° C. for about 2 hours until completion of the reaction The mixture was cooled to about 10° C. and was concentrated by vacuum distillation at about 50° C. to 1.2 L. The temperature was adjusted to 65° C. and n-heptane (820 mL) was slowly added to the stirred mixture over 8 hours at 65° C. The mixture was cooled to 23° C. and then stirred for about 8 hours at room temperature. The resulting solid was isolated by filtration and was washed with a mixture of ethanol/n-heptane (1:1 V:V) followed by n-heptane. The wet product was dried under vacuum at about 50° C. to afford 176 g of lithium salt (86%). $^1$H NMR (400 MHz, DMSO-$d_6$); 9.01 (s, 1H), 7.96 (d, J=7.2 Hz, 3H), 7.79 (d, J=8.0, 1H), 7.34 (d, J=7.6 Hz, 2H), 7.15 (dd, J=8.0, 7.2 Hz, 1H), 3.97 (br d, J=12, 1H), 2.78 (br s, 2H), 2.64 (m, 1H), 1.85 (m, 1H), 1.68-1.61 (m, 2H), 1.42 (s, 9H); $^{13}$C NMR (DMSO-$d_6$, 100.61 MHz); 167.85, 154.35, 148.51, 144.13, 138.48, 130.43, 128.45, 124.05, 122.77, 122.51, 122.32, 79.19, 41.98, 31.68, 28.59, 25.49; HRMS m/z: [M+H]$^+$ Calcd for $C_{24}H_{28}N_3O_4$ 422.2074. Found 422.2068.

Synthesis of (S)-3-(4-(7-carbamoyl-2H-indazol-2-yl)phenyl)piperidin-1-ium 4-methylbenzenesulfonate Monohydrate (Niraparib Tosylate Monohydrate)

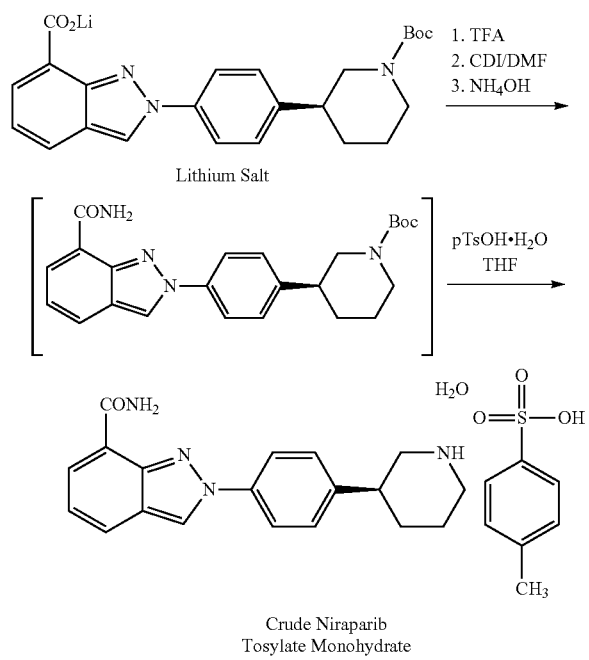

Lithium Salt

Crude Niraparib Tosylate Monohydrate

To a suspension of lithium salt (100 g, 1.0 eq) in dry DMF (420 mL) was added trifluoroacetic acid (28.4 g, 1.06 eq.) slowly at 0-10° C. The mixture was agitated for 30 minutes and carbonyldiimidazole (CDI, 52.8 g, 1.39 eq) was charged portion wise at 0-10° C. The mixture was warmed to about 17-27° C. and was allowed to stir for about 3-4 hours. After the reaction completion, the batch was cooled to 5-10° C. and aqueous ammonium hydroxide solution (27.2 g, ca 29 wt %, and 2.0 eq) was added slowly while maintaining an internal temperature between 5-20° C. The mixture was warmed to 15-23° C. and agitated for about 30 minutes. Water (995 g) was added followed by ethyl acetate (1332 g). The mixture was agitated for at least 30 minutes at 15-25° C., and was allowed to settle. The layers were separated and the organic phase was washed with aqueous ammonium hydroxide (140 mL, ~6%) solution as required to remove any residual Boc heterocyclic acid from the ethyl acetate solution. The organic layer was washed with 5% brine (3×340 mL). The organic phased was concentrated to about 640 mL by vacuum distillation. THF (845 g) was added and vacuum distillation to 640 mL was repeated. The temperature of the solution was cooled to 15-25° C., and para-toluene sulfonic acid monohydrate (pTsOH.H$_2$O) (99.5 g, 2.23 eq) was added. The mixture was stirred at room temperature for about 30 minutes and was refluxed for about 14 hours. Upon the completion of the de-Boc reaction, the mixture was cooled to 17-27° C. and water (89 g) was added. The mixture was stirred for 3-4 hours at about 17-27° C. and the crude product was isolated by filtration. The filter cake was washed with THF and was dried under vacuum at <35° C. to provide crude niraparib tosylate monohydrate (108 g, 91%).

Optical Enrichment

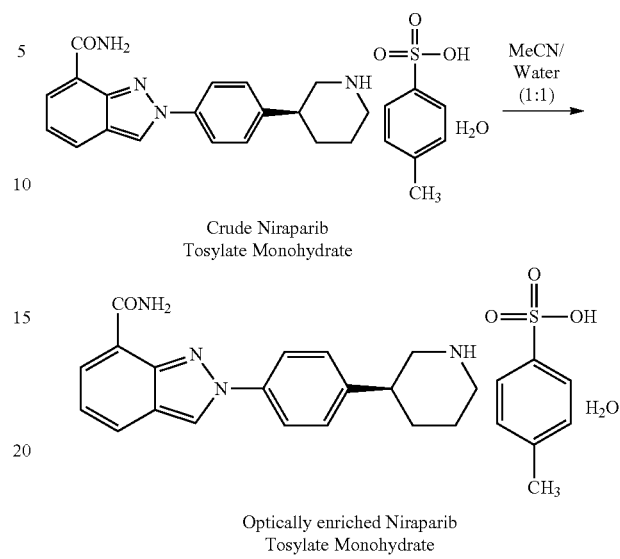

Crude Niraparib Tosylate Monohydrate

Optically enriched Niraparib Tosylate Monohydrate

To a mixture of acetonitrile (1580 g) and of water (2000 g) was added crude niraparib tosylate monohydrate (100 g active enantiomer). The mixture was agitated for about 3 hours at 18-26° C. The mixture was filtered through a cartridge containing activated carbon. The filtrate was concentrated by vacuum distillation at about 45° C. to 1.340 mL. The mixture was cooled to 15-25° C. and held for 1 hour. The product was isolated by filtration and the filter cake was washed with water. The product was dried under vacuum at about 45° C. hours to afford 90 g (87%) of optically enriched niraparib tosylate monohydrate.

Physical Form/Particle Size Adjustment

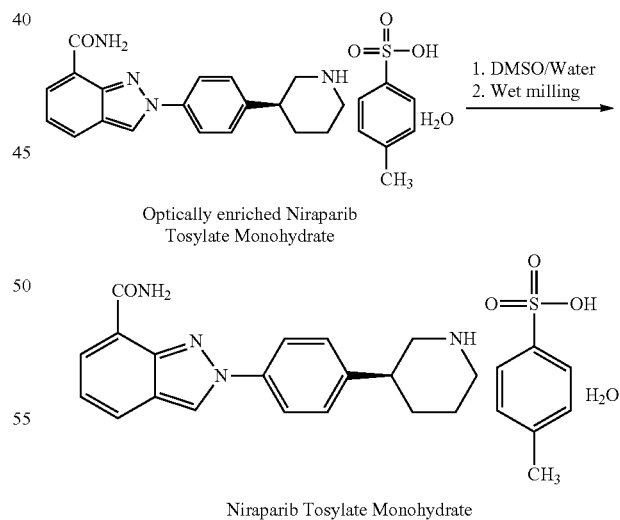

Optically enriched Niraparib Tosylate Monohydrate

Niraparib Tosylate Monohydrate

Water (8.0 L) was charged to a reactor and the temperature was adjusted to 20-30° C. Optically enriched niraparib tosylate monohydrate (1.00 kg) was charged to a second reactor followed by DMSO (4.39 kg). The mixture was stirred and heated to 28-38° C. and agitated until all of the solids had dissolved. This solution was then filtered into the water in the first reactor, while maintaining the temperature of the crystallizer reactor at 20-30° C. The mixture was stirred for 1-2 hour. Optionally, the resulting mixture may be transferred into another reactor through a wet mill if required to reduce the particle size. The mixture was agitated and heated and then slowly cooled. If necessary, this temperature cycling (annealing) can be repeated. The final product was isolated by filtration and the filter cake was washed with water. The wet cake was dried under vacuum at about 45° C. to provide 0.9 kg (90%) of niraparib tosylate monohydrate. $^1$H NMR (400 MHz, CD$_3$OD) 8.97 (s, 1H), 8.15 (dd, J=0.9, 7.1, 2H), 8.04 (d, J=8.6, 2H), 8.01 (dd, J=0.9, 8.4, 2H), 7.72 (d, J=8.1, 2H), 7.51 (d, J=7.9, 2H), 7.27 (dd, J=7.1, 8.4, 2H), 7.22 (d, J=7.7, 4H), 3.49-3.44 (om, 2H), 3.19-3.06 (om, 2H), 3.11 (om, 2H), 2.34 (s, 3H), 2.10-2.09 (om, 2H), 1.94-1.87 (om, 2H); $^{13}$C NMR (100.6 MHz, CD$_3$OD), 169.6, 148.0, 143.6, 143.0, 141.8, 140.4, 131.7, 129.9, 129.7, 127.2, 127.0, 125.3, 124.1, 123.1, 122.3, 121.9, 50.1, 45.1, 41.0, 30.8, 23.9, 21.3; HRMS observed m/z=321.1717 (calculated m/z 321.1710).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A process for preparing a salt of Formula (7),

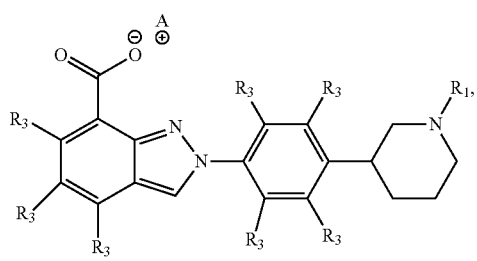

said process comprising:
(a) a first process that is preparing a compound of Formula (1), or a salt thereof, comprising:

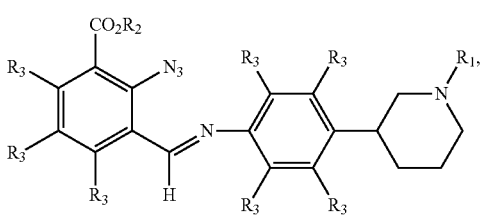

wherein said first process comprises contacting a compound of Formula (2), or a salt thereof, with a compound of Formula (3), or a salt thereof,

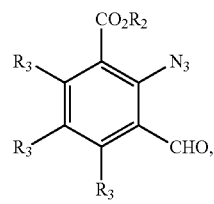

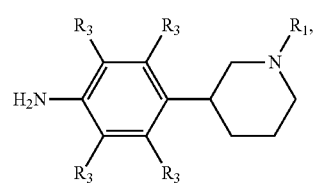

wherein:
R$_1$ is H or an amine protecting group;
R$_2$ is H, C$_{1-10}$ alkyl, C$_1$-10 haloalkyl, or aryl; and
each R$_3$ is independently H, halogen, C$_1$-10 alkyl, C$_1$-10 haloalkyl, or aryl;
(b) a second process that is a process for preparing a compound of Formula (5), or a salt thereof,

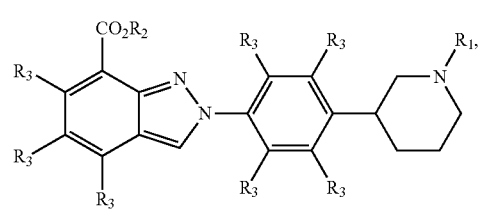

wherein said second process consists of contacting a compound of Formula (1), or a salt thereof, with a copper salt in the presence of THF and toluene solvents,

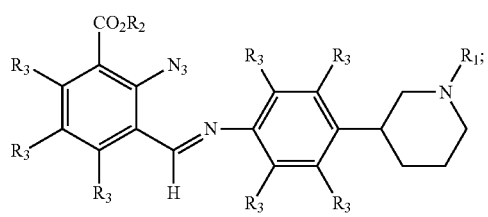

and
(c) a third process that is a process for preparing a salt of Formula (7),

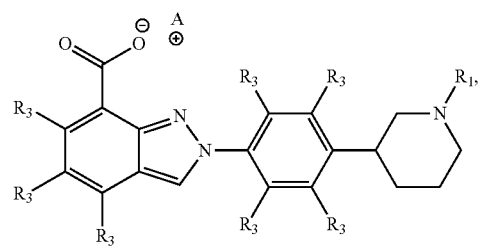

wherein A is a cation, wherein said third process comprises contacting a compound of Formula (5), or a salt thereof, with a metal hydroxide,

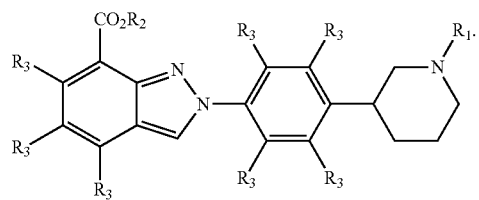

(5)

2. The process of claim 1, wherein the contacting in said first process is in the presence of an acid that is TFA.

3. The process of claim 1, wherein $R_1$ is an amine protecting group that is tert-butyloxycarbonyl group (Boc).

4. The process of claim 1, wherein the compound of Formula (1) has a structure of Formula (4):

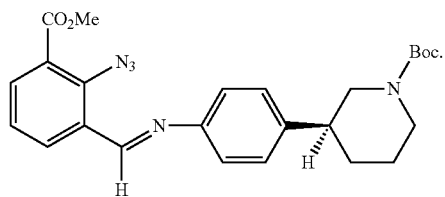

(4)

5. The process of claim 1, wherein the copper salt in said second process is copper(II) trifluoromethanesulfonate (Cu(OTf)$_2$).

6. The process of claim 1, wherein the salt of Formula (7) has a structure of Formula (8):

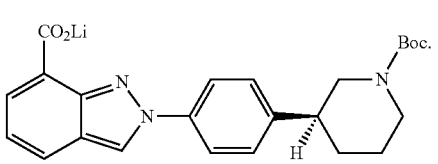

(8)

7. The process of claim 1, wherein the compound of Formula (5) has a structure of Formula (6):

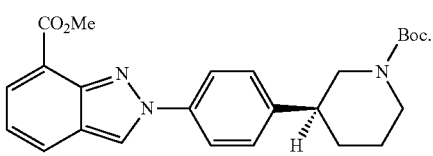

(6)

\* \* \* \* \*

UNITED STATES PATENT AND TRADEMARK OFFICE
CERTIFICATE OF CORRECTION

PATENT NO. : 11,161,834 B2
APPLICATION NO. : 16/608059
DATED : November 2, 2021
INVENTOR(S) : Alistair Stewart et al.

Page 1 of 1

It is certified that error appears in the above-identified patent and that said Letters Patent is hereby corrected as shown below:

In the Claims

In Claim 1, Column 77, Line 55, delete "(I)" and insert -- (1) --, therefor.

In Claim 1, Column 78, Line 41, delete "(I)" and insert -- (1) --, therefor.

In Claim 1, Column 78, Line 43, delete "$R_1$;" and insert -- $R_1$, --, therefor.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*